(12) United States Patent
Hartner et al.

(10) Patent No.: US 7,786,314 B2
(45) Date of Patent: Aug. 31, 2010

(54) PROCESSES FOR PREPARING BICYCLO [3.1.0] HEXANE DERIVATIVES, AND INTERMEDIATES THERETO

(75) Inventors: Frederick W. Hartner, Rahway, NJ (US); Lushi Tan, Rahway, NJ (US); Nobuyoshi Yasuda, Rahway, NJ (US); Naoki Yoshikawa, Rahway, NJ (US)

(73) Assignee: Taisho Pharmaceutical Co., Ltd, Tokyo (JP)

( * ) Notice: Subject to any disclaimer, the term of this patent is extended or adjusted under 35 U.S.C. 154(b) by 927 days.

(21) Appl. No.: 10/578,476

(22) PCT Filed: Nov. 3, 2004

(86) PCT No.: PCT/US2004/036574

§ 371 (c)(1),
(2), (4) Date: Nov. 17, 2006

(87) PCT Pub. No.: WO2005/047215

PCT Pub. Date: May 26, 2005

(65) Prior Publication Data

US 2007/0112030 A1    May 17, 2007

Related U.S. Application Data

(60) Provisional application No. 60/518,391, filed on Nov. 7, 2003.

(51) Int. Cl.
*C07D 319/303* (2006.01)
*C07C 61/00* (2006.01)
*C07C 69/74* (2006.01)

(52) U.S. Cl. .................. 549/336; 549/546; 562/400; 562/457; 560/116; 560/119.1

(58) Field of Classification Search .............. 549/336, 549/546; 562/400, 457; 560/116, 119, 1
See application file for complete search history.

(56) References Cited

U.S. PATENT DOCUMENTS 5,750,566 A    5/1998    Monn et al.

6,160,009 A    12/2000    Massey et al.
6,333,428 B1   12/2001    Nakazato et al.

FOREIGN PATENT DOCUMENTS

| EP | 1000927 A2 | 5/2000 |
| EP | 1164121 A1 | 12/2001 |
| EP | 1 295 862 A1 | 3/2003 |
| WO | WO 02/00595 A1 | 1/2002 |
| WO | 02072525 A1 | 9/2002 |

OTHER PUBLICATIONS

John W. McDonald et al: "Physiological and pathophysiological roles of excitatory amino acids during central nervous system development", Brain Research Reviews, U.K., vo. 15, No. 1, pp. 41-70, Jan.-Apr. 1990.
Darryle Schoepp et al: "Pharmacological and functional characteristics of metabotropic excitatory amino acid receptors", EAA Pharmacology, TiPS, U.K., vol. 11, pp. 508-515, Dec. 1990.
Atsuro Nakazato et al: "Synthesis, SARs, and Pharmacological Characterization of 2-Amino-3 or 6-fluorobicyclo[3.1.0] hexane-2,6-dicarboxylid Acid Derivatives as Potent, Selective, and Orally Active Group II Metabotropic Glutamate Receptor Agonists" American Chemical Society, J. Med. Chem. 2000, 43, pp. 4893-4909.
A. Nakazato et al.; Synthesis, SARs, and Pharmacological Characterization of 2-Amino-3 or 6-fluorobicyclo[3.1.0]hexane-2,6-dicarboxylic Acid Derivatives as Potent, Selective, and Orally Active Group II Metabotropic Glutamate Receptor Agonists; J. Med. Chem. (2000); pp. 4893-4909; vol. 43.
Supplementary European Search Report, Application No. EP 04800646, mailed Dec. 3, 2008.
English Translation of Russian Office Action, Application No. RN 2006119924, mailed Sep. 17, 2008.
English Translation of Russian Office Action, Application No. RN 2006119924, mailed Mar. 30, 2009.
English Translation of Chinese Office Action, Application No. CN 200480038187.9, mailed Apr. 14, 2008.
English Translation of Indian Office Action, Application No. IN 2479/DELNP/2006/10756, mailed Sep. 17, 2008.

*Primary Examiner*—Janet L. Andres
*Assistant Examiner*—Raymond Covington
(74) *Attorney, Agent, or Firm*—Sughrue Mion, PLLC

(57) ABSTRACT

Processes for the preparation of certain [3.1.0]hexane derivatives which are useful as mGluR agonists, and intermediates prepared during such processes.

32 Claims, 2 Drawing Sheets

PROCESSES FOR PREPARING BICYCLO [3.1.0] HEXANE DERIVATIVES, AND INTERMEDIATES THERETO

CROSS-REFERENCE TO RELATED APPLICATIONS

This application claims priority under 35 U.S.C. §119(e) to U.S. provisional application Ser. No. 60/518,391, filed Nov. 7, 2003.

FIELD OF THE INVENTION

The present invention relates to processes for the preparation of bicyclo[3.1.0]hexane derivatives which are useful as metabotropic glutamate receptor modulators. The invention is also related to novel intermediate compounds which are prepared during such processes, and to the hydrochloride salt of (+)-(1R,2S,5S,6S)-2-amino-6-fluoro-4-oxobicyclo[3.1.0] hexane-2,6-dicarboxylic acid, and polymorphs thereof.

BACKGROUND OF THE INVENTION

The excitatory amino acids, including glutamate, modulate a variety of physiological processes in the mammalian central nervous system (CNS), such as long-term potentiation (learning and memory), the development of synaptic plasticity, motor control, respiration, cardiovascular regulation, and sensory perception.

Glutamate acts via at least two distinct classes of receptors. One class is composed of the ionotropic glutamate (iGlu) receptors that act as ligand-gated ionic channels. The second class is the G-protein or second messenger-linked "metabotropic" glutamate (mGluR) receptor. Both classes of receptors appear to mediate normal synaptic transmission along excitatory pathways, and also to participate in the modification of synaptic connections during development and throughout life. Schoepp, Bockaert, and Sladeczek, *Trends in Pharmacol. Sci.*, 11, 508 (1990); McDonald and Johnson, *Brain Research Reviews*, 15, 41 (1990).

Various functionalized bicyclo[3.1.0]hexane derivative compounds have been recognized as mGluR modulators. The mGluR modulators are therapeutically useful for the treatment or prevention of psychiatric disorders, schizophrenia, anxiety and associated diseases, depression, bipolar disorder, and epilepsy; and neurological diseases, such as drug dependence, cognitive disorders, Alzheimer's disease, Huntington's chorea, Parkinson's disease, dyskinesia associated with muscular stiffness, cerebral ischemia, cerebral failure, myelopathy, and head trauma. For example, U.S. Pat. No. 6,333,428, issued Dec. 25, 2001, discloses certain mGluR agonists which are 2-amino-6-fluorobicyclo[3.1.0]hexane derivatives of the formula below:

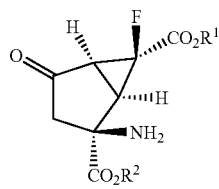

wherein $R^1$ and $R^2$ are each selected from the group consisting of
(1) hydrogen;
(2) $C_{1-10}$ alkyl;
(3) $C_{3-8}$ cycloalkyl; and
(4) $C_{3-8}$ cycloalkyl-$C_{1-5}$ alkyl;

and pharmaceutically acceptable salts thereof. The '428 patent states that the compounds of the invention may be in racemic form, or may be in enantiomeric form. The '428 patent also discloses certain novel intermediates of the formula below:

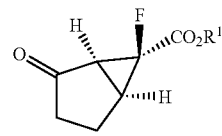

wherein $R^1$ is as defined above.

U.S. Pat. No. 6,160,009, issued Dec. 12, 2000, discloses a class of functionalized bicyclo[3.1.0]hexane derivatives, which are therapeutically useful as mGluR agonists, of the formula below:

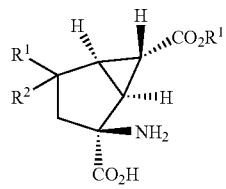

wherein $R^1$ and $R^2$ could together represent =O.

U.S. Pat. No. 5,750,566, issued May 12, 1998, discloses an mGluR agonist of the formula below:

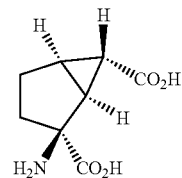

which is known as LY 354740.

Preparation of the mGluR modulators and intermediates disclosed above has been disclosed in the aforementioned patents, in Nakazato et al., *J. Med. Chem.*, 2000, 43, 4893-4909, and in WO 02/00595 (which is published in English as EP 1 295 862). However, the disclosed syntheses involve drawbacks which make them unsuitable for large scale production. For example, the syntheses disclosed in the '428 patent and in Nakazato call for the preparation of racemic intermediates, which must then be subjected to complicated separation procedures involving HPLC, resulting in low productivity. Typically, the known synthetic methods also require the use of expensive and hazardous reagents, such as $Pd(OAc)_2$ and $(PhSe)_2$, which must be present in stoichimetric amounts, and $CH_2N_2$. The synthetic method of Nakazato also requires a harsh hydrolysis using $H_2SO_4$ at high temperatures (145° C.) for five days as the last step of the synthesis, resulting in a low yield, and requires a difficult isolation of the final product from a hydantoin derivative precursor.

It will be appreciated that the mGluR modulators disclosed in U.S. Pat. Nos. 6,333,428, 6,160,009 and 5,570,566, are useful as therapeutic agents. As such, there is a need for a development of a process for the preparation of these compounds, which is readily amenable to scale-up, uses cost-effective and relatively safe reagents, and is therefore capable of practical application to large scale manufacture.

Applicants have now discovered a novel synthesis of a class of enantiomerically pure functionalized bicyclo[3.1.0]hexane derivative mGluR modulators and of enantiomerically pure intermediate compounds.

SUMMARY OF THE INVENTION

The present invention concerns novel processes for the synthesis of a class of functionalized bicyclo[3.1.0]hexane derivative mGluR modulators of formula (I)

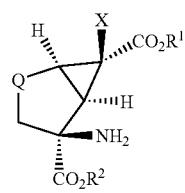

(I)

wherein $R^1$ and $R^2$ are independently selected from the group consisting of
(1) hydrogen,
(2) $C_{1-10}$ alkyl,
(3) $C_{3-8}$ cycloalkyl, and
(4) —$(CH_2)_n$-phenyl wherein n is 1 or 2; and said alkyl, cycloalkyl and phenyl are unsubstituted or substituted with one or more halogen, hydroxy, $C_{1-6}$ alkyl or $C_{1-6}$ alkoxy;

X is selected from the group consisting of
(1) halogen, and
(2) hydrogen; and

Q is —$CH_2$— or —$C(=O)$—;

and pharmaceutically acceptable salts thereof.

The invention further relates to novel processes for the preparation of compounds of formula (II)

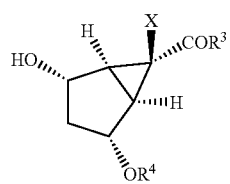

(II)

wherein $R^3$ is selected from the group consisting of
(1) —OH,
(2) —O—$R^a$, and
(3) —$NR^bR^c$,
wherein $R^a$ is selected from the group consisting of
(a) $C_{1-10}$ alkyl, and
(b) $C_{3-8}$ cycloalkyl,
and $R^a$ is unsubstituted or substituted with one or more
(i) $C_{1-10}$ alkoxy,
(ii) hydroxy,
(iii) halogen,
(iv) $SR^d$, (v) aryl, unsubstituted or substituted with one or more hydroxy, $C_{1-10}$ alkoxy, $C_{1-10}$ alkyl or halogen,
(vi) heteroaryl, unsubstituted or substituted with one or more hydroxy, $C_{1-10}$ alkoxy, $C_{1-10}$ alkyl or halogen, and
(vii) $NR^eR^f$;

$R^b$, $R^c$, $R^e$ and $R^f$ are selected from the group consisting of
(a) hydrogen,
(b) $C_{1-10}$ alkyl, and
(c) $C_{3-8}$ cycloalkyl,
and when $R^b$, $R^c$, $R^e$ or $R^f$ are $C_{1-10}$ alkyl or $C_{3-8}$ cycloalkyl, said $C_{1-10}$ alkyl
and $C_{3-8}$ cycloalkyl are unsubstituted or substituted with one or more
(i) hydroxy,
(ii) $C_{1-10}$ alkoxy,
(iii) $SR^d$,
(iv) aryl, unsubstituted or substituted with one or more hydroxy, $C_{1-10}$ alkoxy, $C_{1-10}$ alkyl or halogen, and
(v) heteroaryl, unsubstituted or substituted with one or more hydroxy, $C_{1-10}$ alkoxy, $C_{1-10}$ alkyl or halogen, and
(vi) $NR^gR^h$;

wherein $R^g$ and $R^h$ are hydrogen, $C_{1-10}$ alkyl or $C_{3-8}$ cycloalkyl;

or $R^b$ and $R^c$, together with the N atom to which they are attached, form a group

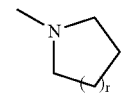

wherein r is 1 or 2, and the $NR^bR^c$ group may be unsubstituted or substituted at the ring carbon atoms by one or more
(i) hydroxy,
(ii) $C_{1-10}$ alkoxy,
(iii) $SR^d$,
(iv) aryl, unsubstituted or substituted with one or more hydroxy, $C_{1-10}$ alkoxy, $C_{1-10}$ alkyl or halogen, and
(v) heteroaryl, unsubstituted or substituted with one or more hydroxy, $C_{1-10}$ alkoxy, $C_{1-10}$ alkyl or halogen, and
(vi) $NR^gR^h$,
$R^d$ is hydrogen or $C_{1-10}$ alkyl;

X is selected from the group consisting of
(1) halogen, and
(2) hydrogen; and $R^4$ is selected from the group consisting of
(1) hydrogen,
(2) $C_{1-10}$ alkyl,
(3) Si—$(R^9)(R^{10})(R^{11})$,
(4) $C(=O)$—$R^{12}$,
(5) $CH_2$-phenyl, wherein said phenyl is unsubstituted or substituted with one or more substituents selected from the group consisting of nitro, halogen, $C_{1-10}$ alkyl and $C_{1-10}$ alkoxy,
(6) $(CH_2)_p$—O—$(CH_2)_q$—X'—$R^{14}$,
(7) tetrahydropyranyl,
wherein $R^9$, $R^{10}$ and $R^{11}$ are each $C_{1-10}$ alkyl or phenyl, and $R^{14}$ is selected from the group consisting of
(a) hydrogen,
(b) $C_{1-10}$ alkyl, p is 1 or 2;
q is an integer of from 1-10; and
X' is O or a bond;

and salts thereof.

The invention is also related to novel processes for the preparation of compounds of formula (XII)

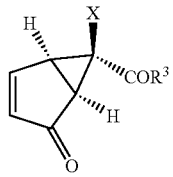
(XII)

or its enantiomer (XII')

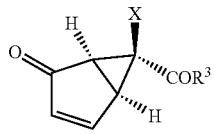
(XII')

wherein $R^3$ and X are as defined above, and salts thereof.

Compounds of formulas (II), (XII) and (XII') are intermediates prepared in the synthesis of the mGluR modulators of formula (I). Processes for using compound (XII) or (XII') to form mGluR modulators of formula (I) are disclosed in the aforementioned '566, '428 and '009 patents, and in Nakazato et al., *J. Med. Chem.*, 2000, 43, 4893-4909. The invention also relates to certain novel intermediates which are prepared during the synthesis of the invention.

BRIEF DESCRIPTION OF THE DRAWINGS

The invention is described in connection with the appended drawings, in which.

DETAILED DESCRIPTION OF THE INVENTION

Figure 1:
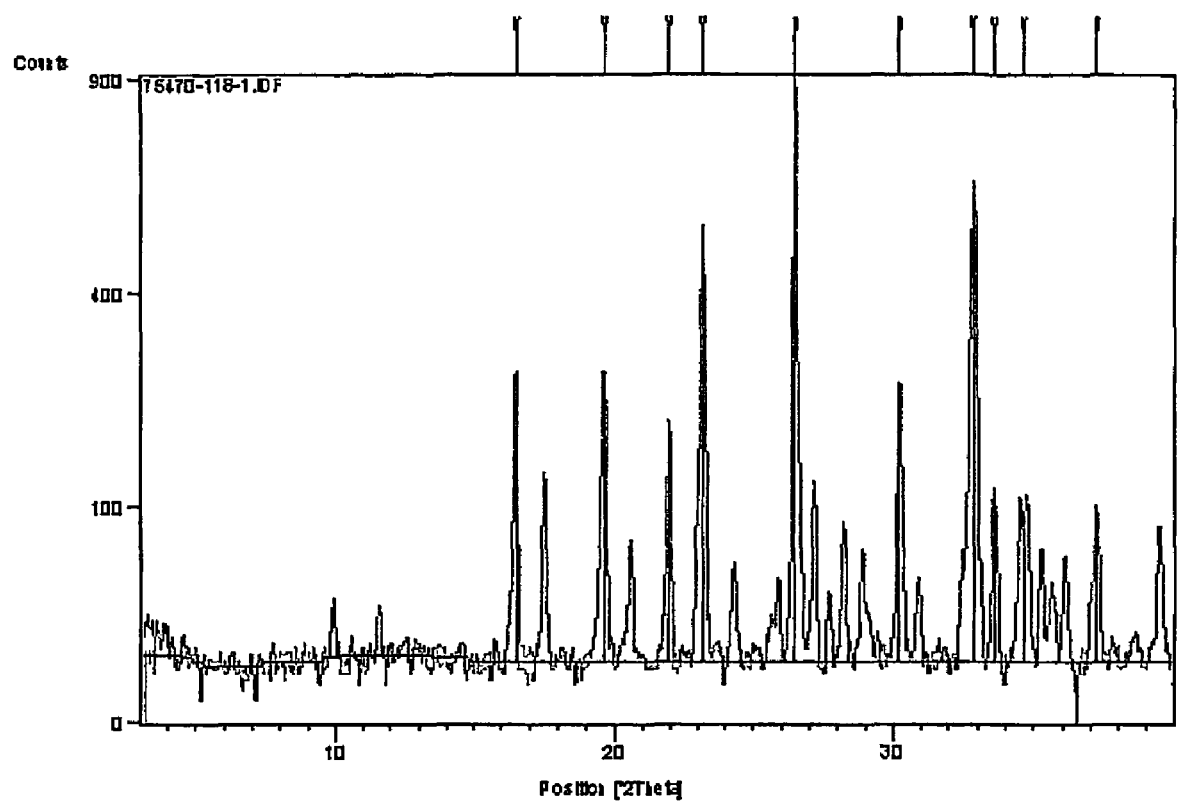
FIG. 1 is the x-ray powder diffraction (XPRD) pattern of a crystal form of the hydrochloride salt of (+)-(1R,2S,5S,6S)-2-amino-6-fluoro-oxobicyclo[3.1.0]hexane-2,6-dicarboxylic acid.

The present invention is directed to processes for preparing functionalized bicyclo[3.1.0]hexane derivatives of formula (I)

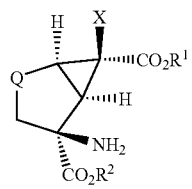
(I)

wherein $R^1$ and $R^2$ are independently selected from the group consisting of
(1) hydrogen,
(2) $C_{1-10}$ alkyl,
(3) $C_{3-8}$ cycloalkyl, and
(4) $(CH_2)_n$-phenyl, wherein n is 1 or 2, and said alkyl, cycloalkyl and phenyl are unsubstituted or substituted with one or more halogen, hydroxy, $C_{1-6}$ alkyl or $C_{1-6}$ alkoxy;

X is selected from the group consisting of
(1) halogen, and
(2) hydrogen; and

Q is $—CH_2—$ or $—C(=O)—$;

and pharmaceutically acceptable salts thereof.

In one embodiment, the invention is directed to a process for preparing compounds of formula (IA):

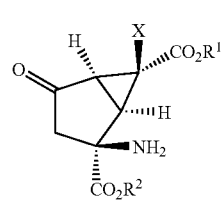
(IA)

wherein X, $R^1$ and $R^2$ are as defined above.

In this embodiment, the invention comprises oxidizing an intermediate compound of formula (II):

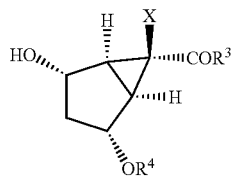
(II)

wherein X, $R^3$ and $R^4$ are as defined above;
to form a compound of formula (IV):

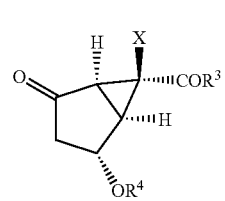
(IV)

deprotecting the hydroxyl group of the compound of formula (IV) to form a compound of formula (V):

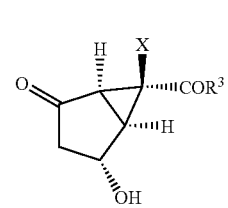
(V)

and reacting the compound of formula (V) with the compound of formula (VI)

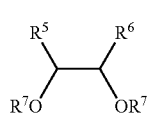
(VI)

wherein each $R^5$ and $R^6$ is independently selected from the group consisting of
(1) hydrogen,
(2) $C_{1-10}$ alkyl,
(3) $C_{3-8}$ cycloalkyl, and
(4) $(CH_2)_m$-phenyl, wherein m is 0, 1 or 2, and $R^7$ is selected from the group consisting of
(1) hydrogen, and
(2) Si—$(R^9)(R^{10})(R^{11})$, wherein $R^9$, $R^{10}$ and $R^{11}$ are each $C_{1-10}$ alkyl or phenyl;
to give a compound of formula (VII):

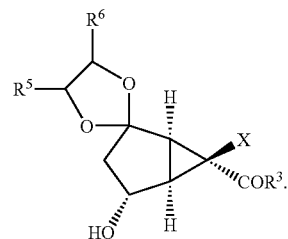
(VII)

The compound of formula (VII) is then oxidized to give a compound of formula (VIII):

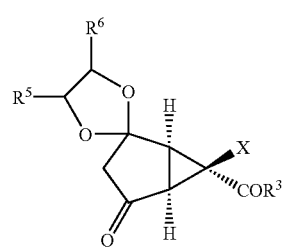
(VIII)

which is converted to a compound of formula (IX):

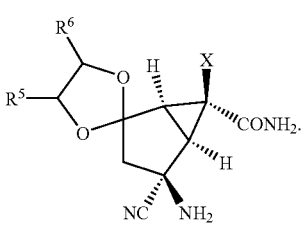
(IX)

The compound of formula (IX) is then converted to the desired compound of formula (IA):

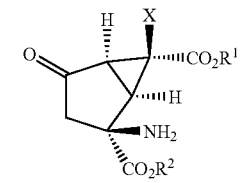
(I)

wherein X, $R^1$ and $R^2$ are as defined above.

In preferred embodiments of the process of preparing compounds of formula (IA), X is fluoro. In other preferred embodiments, X is hydrogen.

In preferred embodiments of the process of making compounds of formula (IA), $R^1$ and $R^2$ are hydrogen.

In preferred embodiments of the process of preparing compounds of formula (IA), $R^3$ is methoxy, ethoxy or benzyloxy.

In the process of preparing compounds of formula (IA), preferred $R^4$ groups are TBS, TMS and TES. A preferred $R^7$ group is TMS.

In preferred embodiments of the process of preparing compounds of formula (IA), $R^5$ and $R^6$ are selected from the group consisting of methyl and phenyl. It is preferred that $R^5=R^6$.

In preferred embodiments of the process of preparing compounds of formula (IA), the step of converting compound (IX) to compound (I) comprises hydrolysis of compound (IX).

The invention is also directed to novel intermediate compounds of formulas (VII), (VIII) and (IX):

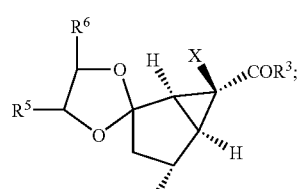
(VII)

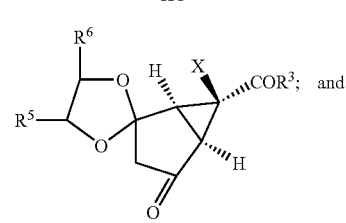
(VIII) and

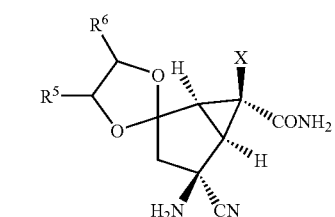
(IX)

which are prepared during the synthesis of the mGluR modulators of formula (I); and salts thereof. In compounds (VII), (VI) and (IX), $R^3$, $R^5$, $R^6$ and X are as defined above.

The present invention is also directed to processes for preparing the intermediate compounds of formula (II):

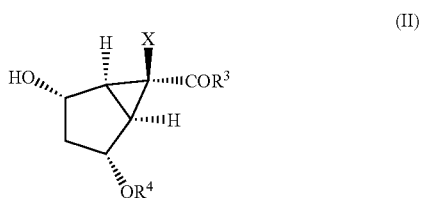

wherein $R^3$, X and $R^4$ are as defined above, and salts thereof. In this process, a compound of formula (X):

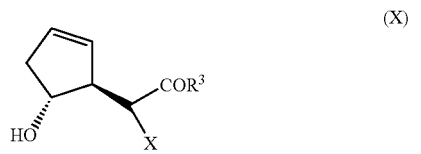

wherein X is hydrogen and $R^3$ is as defined above, is subjected to epoxidation, for example by reaction with a peroxide such as tert-butyl hydroperoxide, or other oxidants (including peracids such as perbenzoic acid and peracetic acid) preferably in the presence of a metal catalyst, such as $VO(acac)_2$. The hydroxy group of compound (X) may then be protected, for example with TBS or TMS, to result in a compound of formula (XI):

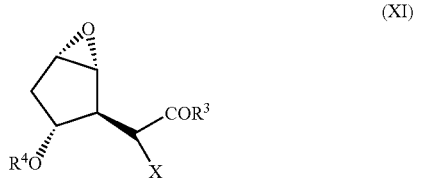

wherein X is hydrogen and $R^4$ is as defined above. The compound may then be fluorinated (wherein X is fluorine). Alternatively, compound (X) may first be fluorinated (wherein X is F). The fluorinated compound may then be subjected to epoxidation as described above.

Alternatively, formation of the epoxide derivative may occur via halohydrin, by reaction with a halogen source. For example, a compound of formula (X) may be reacted with N-bromo succinimide, followed by treatment with a base, and the epoxide product is then isolated.

The protected epoxide derivative (XI) is then reacted with a suitable base in the presence of a Lewis Acid to afford a compound of formula (II):

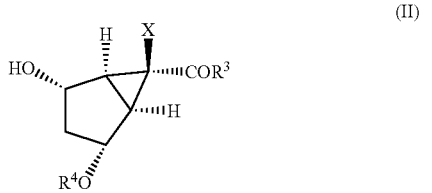

wherein X, $R^3$ and $R^4$ are as defined above. Compound (II) may then be oxidized to give compound (IV):

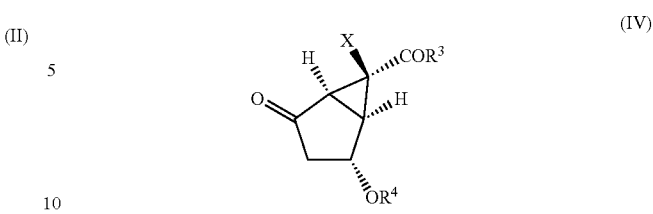

which may then be converted according to the process steps described above, to form compounds of formula (IA).

Alternatively, compounds of formula (IV) may be converted to compounds of formula (IA) according to methods described in the prior art. For example, Nakazato, *J. Med. Chem.* 2000, 43, 4893-4909 describes the use of a compound of formula (IV) to form a compound of formula (IA) in Scheme 5 at page 4898. The process taught by Nakazato requires formation of a dithioketal, followed by hydantoin derivative.

U.S. Pat. No. 6,160,009 describes the use of a compound of formula (IV) to form a compound of formula (IA) at columns 8-13. The reaction proceeds via a hydantoin derivative.

In preferred embodiments of the process of preparing compounds of formula (II), $R^3$ is methoxy, ethoxy or benzyloxy.

In preferred embodiments of the process of preparing compounds of formula (II), X is fluoro. In other preferred embodiments, X is hydrogen.

In the process of preparing compounds of formula (II), preferred $R^4$ groups are TBS, TMS and TES.

In other preferred embodiments of the process, the oxidation of compound (II) comprises contacting compound (II) with $RuCl_3$ and an oxidizing agent. Preferred oxidizing agents are bleaches. A preferred bleach is NaClO.

The invention is also directed to novel intermediate compounds of formulas (XA), (XI), (IVA) and (II), as depicted below:

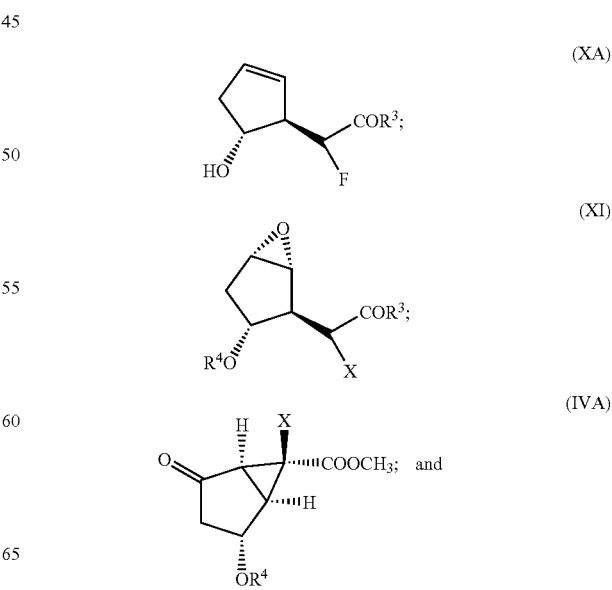

-continued

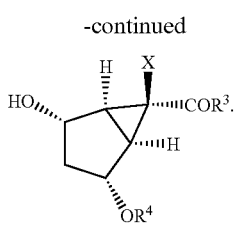
(II)

In compounds (XA), (XI), (IVA) and (II), $R^3$, X and $R^4$ are as defined above.

The invention is also directed to processes for preparing intermediate enone compounds of formula (XII):

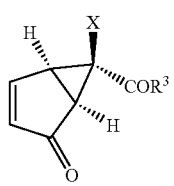
(XII)

and its enantiomer (XII'):

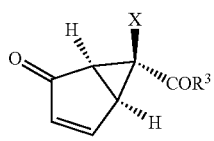
(XII')

wherein $R^3$ and X are as defined above; and salts thereof.

In an embodiment of this process for preparing a compound of formula (XII), a compound of formula (II)

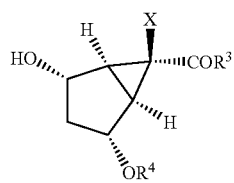
(II)

wherein X, $R^3$ and $R^4$ are as defined above, is subjected to a reaction to form a compound of formula (XII), having a leaving group $R^8$ as follows:

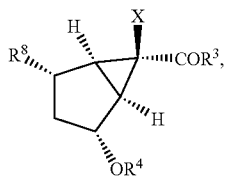
(XIII)

wherein $R^8$ is selected from the group consisting of
(1) halogen, and
(2) $O\text{—}SO_2\text{—}R^{12}$ wherein $R^{12}$ is selected from the group consisting of (a) $C_{1-10}$ alkyl,
(b) $C_{1-10}$ perfluoroalkyl,
(c) phenyl which is substituted or unsubstituted with one or more substituents selected from the group consisting of nitro, halogen, $C_{1-10}$ alkyl, or $C_{1-10}$ alkoxy.

Thereafter, the $R^4$ group is removed to afford the hydroxy ester derivative (XIV) below:

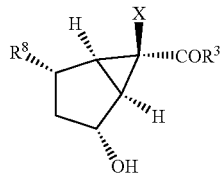
(XIV)

which is then oxidized to afford the desired [3.1.0]-bicyclic-α, β unsaturated ketone of formula (XII):

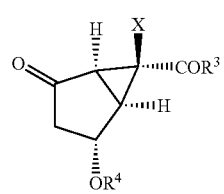
(XII)

In an embodiment of this process for forming a compound of formula (XII'), a compound of formula (II) is oxidized to form a compound of formula (IV)

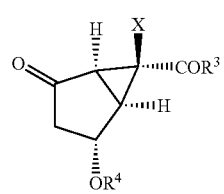
(IV)

wherein X, $R^3$ and $R^4$ are as defined above. Compound (IV) is then subjected to an elimination reaction, for example by reaction with a base such as DBU, to give a compound of formula (XII')

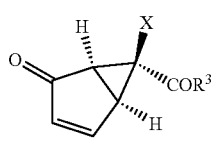
(XII')

which is the enantiomer of the corresponding compound of formula (XII).

The enone compound of formula (XII) or (XII') may be converted to a compound of formula (I) according to methods known in the prior art. For example, Nakazato, *J. Med. Chem.* 2000, 43, 4893-4909 describes the use of a compound of formula (XII) to form a compound of formula (IA) in Scheme 5 at page 4898.

U.S. Pat. No. 5,750,566 describes the use of a compound of formula (XII) to form compounds of formula (I) wherein Q is $CH_2$, at column 12 in Scheme IV.

Dominguez et al, *Tetrahedron: Asymmetry,* 1997, 8, 511-514 describes the use of a compound of formula (XII) to form compounds of formula (I) wherein Q is $CH_2$, at Scheme 2 at page 513. The process requires formation of a hydantoin derivative.

In preferred embodiments of the synthesis of compounds of formula (XII) and (XII'), $R^3$ is methoxy, ethoxy or benzyloxy.

In preferred embodiments of synthesis of compounds of formula (XII) and (XII'), X is fluoro. In other preferred embodiments, X is hydrogen.

In the synthesis of compounds of formula (XII) and (XII'), preferred $R^4$ protecting groups are TBS, TMS and TES.

In the synthesis of compounds of formula (XII) and (XII'), preferred $R^8$ groups include O-tosyl (para toluenesulfonyl), O-mesyl and O-triflate.

The invention is also directed to the hydrochoride salt of compounds of formula (I). In preferred embodiments, the hydrochloride salt is the salt of the compound of formula (I) wherein X is fluoro and $R^1$ and $R^2$ are both hydrogen, denoted compound (I'):

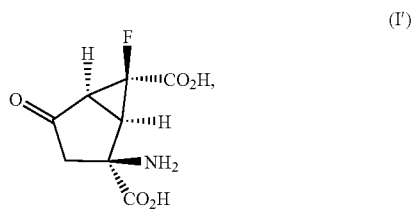

which is (+)-(1R,2S,5S,6S)-2-amino-6-fluoro-4-oxobicyclo[3.1.0]hexane-2,6-dicarboxylic acid. The invention is also directed to a novel crystal polymorph of the hydrochloride salt of compound (I').

DEFINITIONS

As used herein, the term "Strecker synthesis reaction" or "Strecker reaction" refers to a reaction known to those skilled in the art of organic synthesis, to prepare alpha amino nitriles As used herein, the term "substantially enantiomerically pure form" means that the desired enantiomer is present in at least 50% e/e (enantiomeric excess) relative to the undesired enantiomer.

As used herein, the term "Lewis Acid" refers to a compound which is capable of accepting electrons.

As used herein, the term "aryl" refers to a polyunsaturated aromatic hydrocarbon substituent, which can be a single ring or multiple rings (preferably from 1 to 3 rings) which can be fused together or linked covalently. Non-limiting examples of aryl groups include phenyl, naphthyl and biphenyl.

As used herein, the term "heteroaryl" refers to a polyunsaturated aromatic ring having at least one heteroatom (nitrogen, oxygen or sulfur) in the ring chain. A heteroaryl group can be a single ring or multiple rings (preferably from 1 to 3 rings) which can be fused together or linked covalently. Non-limiting examples of heteroaryl groups include pyrole, pyrazole, imidazole, pyridine, pyrazine, pyrimidine, furan, pyran, oxazole, isoxazole, purine, benzimidazole, quinoline, isoquinoline, indole and the like.

When a heteroaryl group as defined herein is substituted, the substituent may be bonded to a ring carbon atom of the heteroaryl group, or to a ring heteroatom (i.e., a nitrogen, oxygen or sulfur), which has a valence which permits substitution. Preferably, the substituent is bonded to a ring carbon atom.

As used herein, the term "halogen" refers to fluorine, chlorine and bromine. A preferred halogen is fluorine.

As used herein, the term "alkyl," by itself or as part of another substituent, means a straight or branched chain hydrocarbon radical having the number of carbon atoms designated (e.g., $C_{1-10}$ alkyl means an alkyl group having one to ten carbon atoms). Examples of alkyl groups include methyl, ethyl, n-propyl, isopropyl, n-butyl, t-butyl, isobutyl, sec-butyl, pentyl, hexyl and the like.

As used herein, the term "alkoxy," by itself or as part of another substituent, means the group O-alkyl, wherein alkyl is as defined above, to include straight or branched alkyl groups.

As used herein, the term "cycloalkyl," by itself or as part of another substituent, means a saturated cyclic hydrocarbon radical having the number of carbon atoms designated (e.g., $C_{3-8}$ cycloalkyl means a cycloalkyl group having three to eight carbon atoms).

As used herein, the term "pharmaceutically acceptable" refers to molecular entities and compositions that are "generally regarded as safe," e.g., that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and, more particularly, in humans.

In one embodiment, the process of the invention is depicted in Scheme 1 below.

Scheme 1

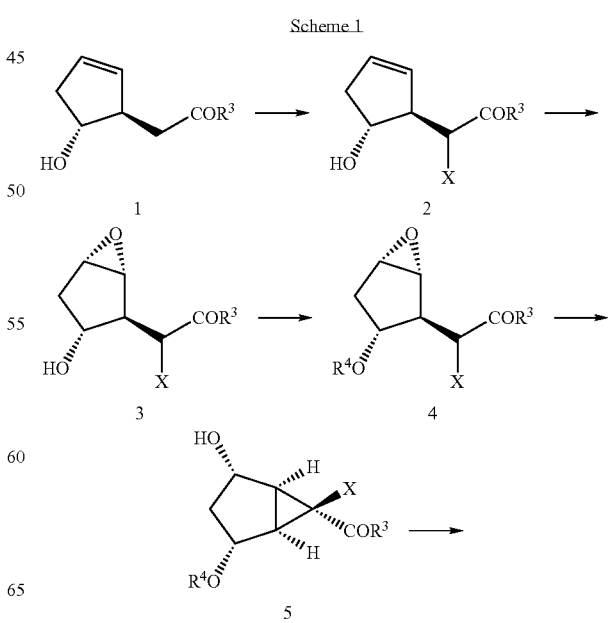

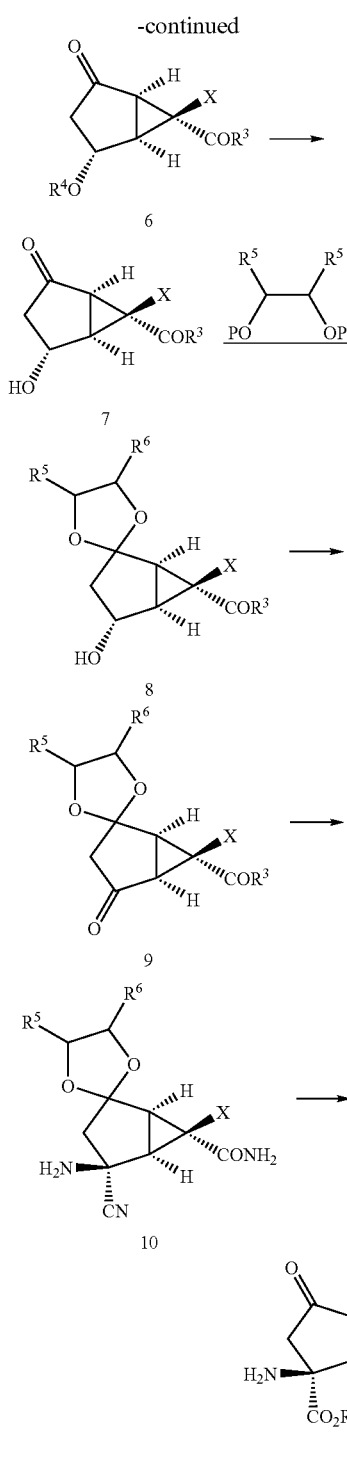

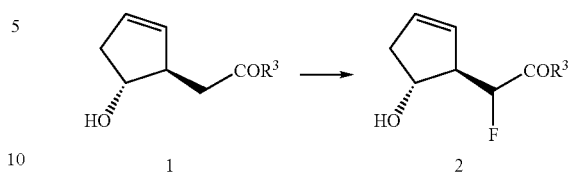

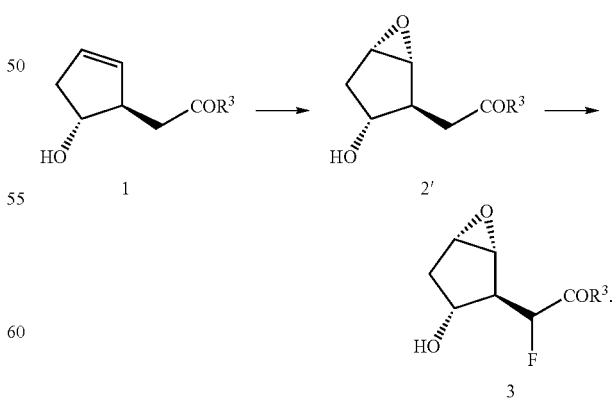

wherein $R^1$, $R^2$, $R^3$, $R^4$, $R^5$, $R^6$, $R^7$, $R^8$ and X are as defined above.

The optically active trans hydroxy ester 1 may be obtained according to the teachings of Partridge et al., *Org. Synth* 1985, 83, 44. See also Tolstikov et. al, *J. Org. Chem. USSR* 1989, 25(1.2) and 1990, 26 (7.1, 1274). The trans hydroxy ester 1 is preferably more than 90% e/e, more preferably more than 95% e/e, even more preferably more than 96% e/e.

The trans hydroxy ester 1 may be fluorinated without protecting the secondary alcohol, to give compound 2.

One method of achieving the desired fluorination is by reaction with the fluorinating agent, such as N-fluorobenzenesulfonimide (NFSI) with a strong base in a suitable solvent, for example tetrahydrofuran. It is preferred that the reaction occur at temperatures of less than −65° C., preferably less than −75° C., most preferably less than −78° C. Suitable strong bases include lithium diisopropylamide (LDA), lithium tetramethylpiperizide, lithium hexamethyldisilazide (LHMDS), or corresponding potassium or sodium salts.

Stereoselective epoxidation of 2 may then be achieved by reaction in toluene with an oxidizing agent, such as a peroxide derivative (for example tert-butyl hydroperoxide), and a catalyst (for example, a catalytic amount of vanadyl acetylacetonate (VO(acac)$_2$). It is preferred that the reaction occur at from about 0° C. to about 40° C.

Alternative oxidizing agents include meta chloroperoxybenzoic acid (mCPBA). The resulting epoxide 3 is obtained as a trans isomer.

Alternatively, the trans hydroxy ester 1 may be first subjected to stereoselective epoxidation, and the resulting epoxide 2' may be fluorinated to yield compound 3.

Epoxidation may also be obtained by treatment of 1 (or fluorinated compound 2) with a halogenating agent, for example NBS or NIS, in a suitable solvent (for example, a mixture of DMSO and water). Compound 1 then forms a halohydrin derivative, which is cyclized with a base (such as DBU) to form the epoxide.

Protection of the hydroxyl group of 3 with a protecting agent R⁴, for example a silyl protecting agent such as tert butyldimethylsilyl chloride (TBSCl) under suitable conditions, for example in imidazole and DMF, produces the protected epoxide compound 4, as shown below:

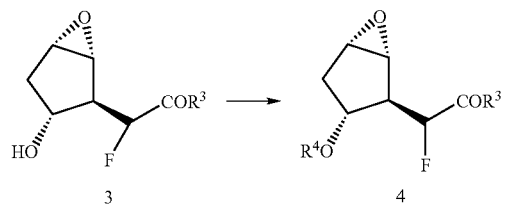

The protected epoxide 4 may then be subjected to an intramolecular epoxide opening cyclopropanation reaction. The reaction proceeds with addition of a base in the presence of a Lewis Acid, such as Et₃Al. Preferably, the reaction occurs at about −50° C.

In a preferred embodiment, compound 4 is first treated with Et₃Al and LiHMDS is then added dropwise. The reaction may proceed for 0.5 to 6 hours, at a temperature of from −20° C. to −80° C. A preferred time is about 1 hour. A preferred temperature is about −60° C. Alternative Lewis Acids which may be used in the reaction include, RTi(OR)₃, R₂Ti(OR)₂, RAlX₂ or R₂AlX, wherein X is a halogen or an inorganic radical and each R is a hydrocarbon group. Exemplarly Lewis Acids include Al(OiPr)₃, Ti(OiPr)₄, BF₃ etherate, Et₂Zn, Et₃Al and Sc(OTf)₃. Compound 5 is obtained in the desired stereoisomeric form.

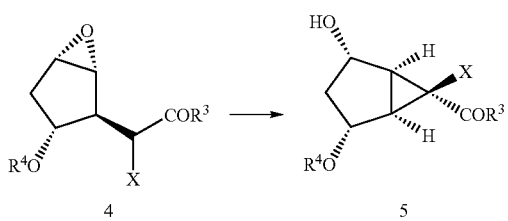

Oxidation of the resulting free alcohol and removal of the protecting group provides bicyclic hydroxy ketone 7 (compound II). Preferred oxidizing agents include reagent grade sodium hypochlorite solution or commercial bleach. The reaction may proceed in the presence of a catalytic amount of RuCl₃ and in the presence of acetic acid (1.5 equivalents) at 0° C. in acetonitrile. The excess sodium hypochlorite should then be removed (for example, by quenching with isopropyl alcohol). The addition of an acid (e.g., 20 mol % of 1M HCl) to the acetonitrile solution cleaves the protecting group R⁴.

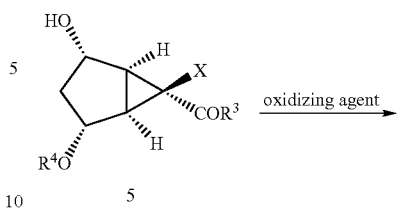

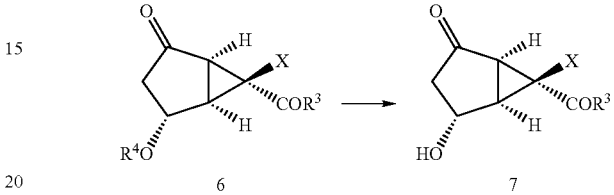

Compound 7 may be protected as a ketal 8, by reaction with diol derivatives. A preferred R⁷ group is TMS.

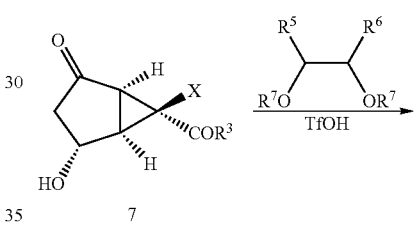

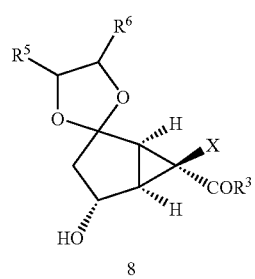

The reaction proceeds in the presence of acid (e.g., 0.1 equivalent), at from about 0° C. to about −10° C. A preferred acid is TfOH or TfOTMS.

Oxidation of the secondary alcohol of 8 yields ketone 9.

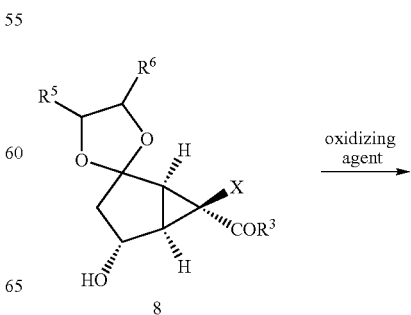

-continued

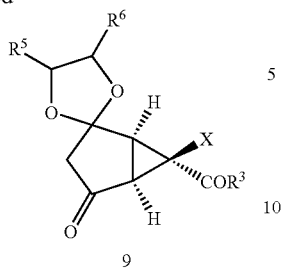

9

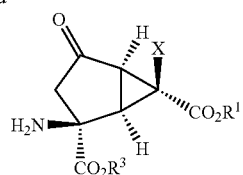

11

The oxidation reaction may proceed with any oxidizing conditions such as Swern conditions. Alternatively, the oxidation may proceed in the presence of $RuCl_3$ (0.5 mol %), with NaClO in acetonitrile and acetic acid, at from 0° C. to room temperature.

Compound 9 is then subjected to a Strecker reaction with ammonia. The reaction may proceed in an alcohol solvent (e.g., methanol) with ammonia at room temperature.

The hydrolysis reaction may proceed in 5 hours using a 1:3 mixture of acetic acid and 8 M HCl at 75° C. Alternatively, the reaction may proceed in the presence of 60% $H_2SO_4$, at about 100° C., for about 2 hours, or alternatively by treatment with acetic acid/$H_2SO_4$ at 60° C., for about 2 hours.

Thereafter, the desired compound 11 may be isolated as the hydrochloride salt, according to methods known to those skilled in the art.

In another embodiment, the process of the invention is depicted in Scheme 2 below.

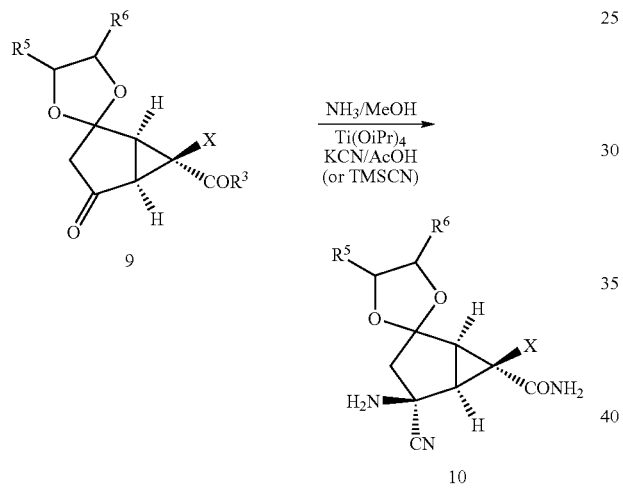

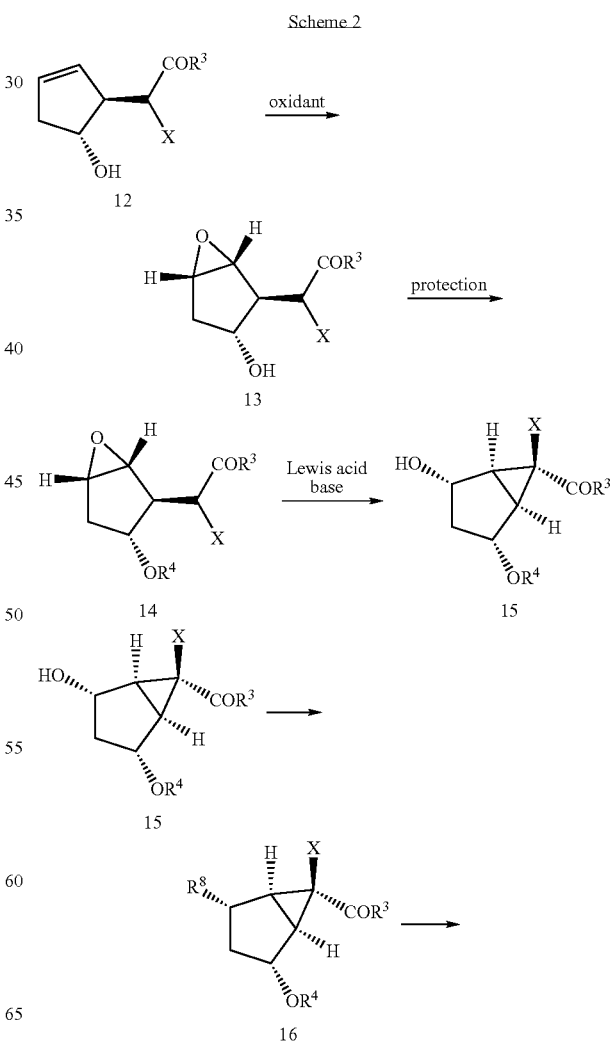

Subsequently, TMSCN may be added at from −10° C. to 0° C. TMSCN can be replaced with KCN/NaCN in the presence of acids. A titanium compound, such as titanium isopropoxide ($Ti(OiPr)_4$), may be used to promote the reaction. The reaction yields the desired amino-nitrile 10 with high diastereoselectivity.

Compound 10 is then subjected to hydrolysis to provide the desired 2-amino-6-fluorobicyclo[3.1.0]hexane (compound 11).

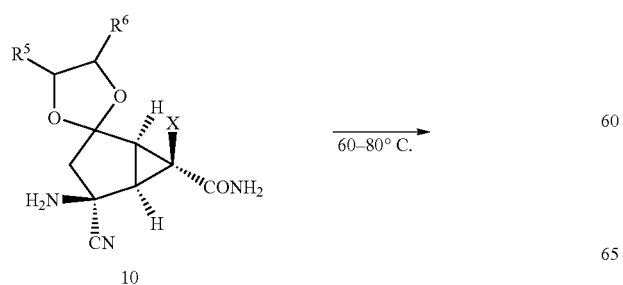

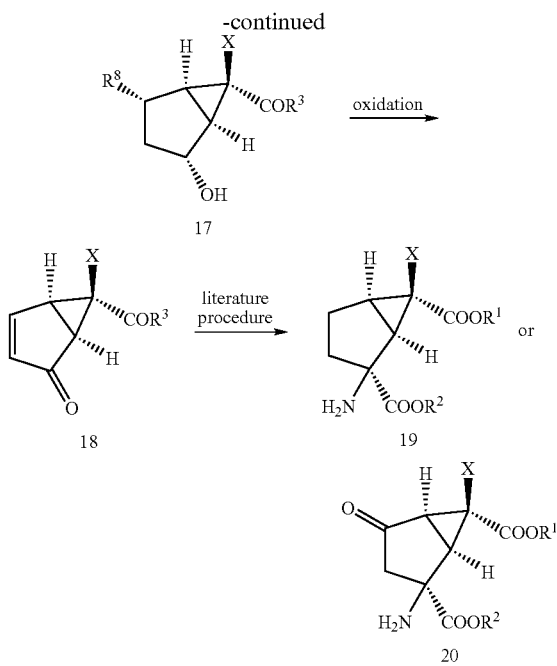

wherein X, $R^3$, $R^4$ and $R^8$ are as defined above.

In Scheme 2, optically active trans-hydroxy ester 12 was obtained as taught above in the description of scheme 1. Epoxidation of 12 proceeded in a diastereoselective manner to afford epoxide 13, protection of the hydroxyl group in 13 gave 14, and treatment of 14 with a Lewis acid followed by a base produced a bicyclo[3.1.0] compound 15. The use of the enantiomer of 12, which is disclosed in Partridge et al., *Org. Synth* 1985, 83, 44, will afford the synthesis of the enantiomers of 13, 14, and 15.

The mono-protected [3.1.0]bicyclic diol 15 (which is identical to 5 from scheme 1) is transformed to a [3.1.0]bicyclic α,β-unsaturated ketone. In this scheme, the hydroxyl group in the alcohol 15 is converted to a leaving group $R^8$, and the protecting group $R^4$ is removed to afford hydroxy ester 17. Suitable $R^8$ leaving groups include sulfonate (for example, para-toluenesulfonate) and halides. Oxidation of 17 is induced by the elimination of the $R^8$ leaving group to afford a [3.1.0]bicyclic α,β-unsaturated ketone 18, which can be used for the synthesis of mGluR agonists 19 (which is identical to 11 from scheme 1) and 20, according to the teachings of U.S. Pats. Nos. 5,750,566, 6,333,428 and 6,160,009, and Nakazoto et al., *J. Med. Chem.*, 2000, 43, 4893-4909.

In another embodiment, the process of the invention is depicted in scheme 3 below:

Scheme 3

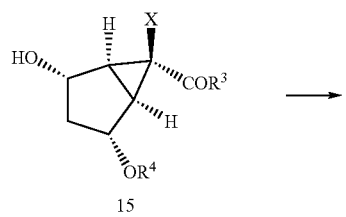

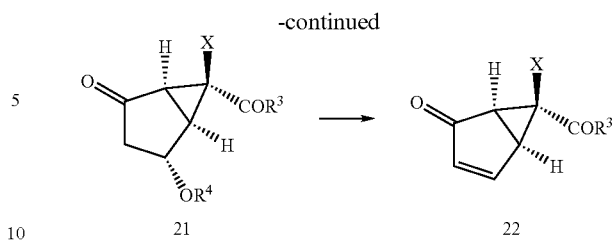

wherein X, $R^3$ and $R^4$ are as defined above. Scheme 3 depicts a synthesis of the enantiomer of enone 18 (from scheme 2).

The chemical structures described above include each of the enantiomers either in enantiomerically pure form or in mixture form.

The starting materials and reagents for the processes described herein are either commercially available or are known in the literature or may be prepared following literature methods described for analogous compounds. The skills required in carrying out the reaction and purification of the resulting reaction products are known to those in the art. Purification procedures include crystallization, distillation, normal phase or reverse phase chromatography.

The following examples are provided for the purpose of further illustration only and are not intended to be limitations on the disclosed invention. Examples 1-10 illustrate the method of scheme 1. Examples 11-15 illustrate the method of scheme 2. Examples 16 and 17 illustrate the method of scheme 3.

Example 1

Methyl fluoro[(1R,5R)-5-hydroxycyclopent-2-en-1-yl]acetate 2

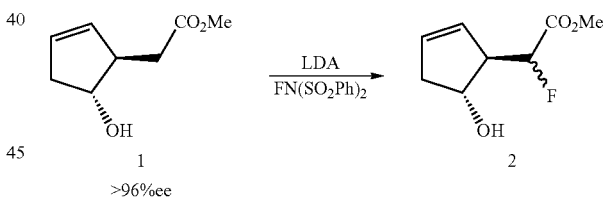

To a solution of diisopropylamine (10.8 mL, 76.8 mmol) in THF (28 mL), was added a solution of butyllithium (28.2 mL, 70.4 mmol, 2.5 M in hexanes) over 40 min while the inside temperature was maintained between 0° C. and 5° C. The resulting solution was stirred at 0° C. for 3 min before cooled to −78° C. by dry ice-acetone bath. A solution of ester 1 (5.00 g, 32.0 mmol) in THF (41.3 mL) was added dropwise to the LDA solution over 45 min while the inside temperature was maintained below −73° C., and the resulting solution was stirred at −78° C. for 20 min to form an orange (or dark orange) solution of dianion. A separate flask was charged with N-fluorobenzenesulfonimide (14.1 g, 44.8 mmol) and THF (62 mL), and the resulting solution was cooled to −96° C. by liquid nitrogen-acetone bath. The solution of the dianion was added via an addition funnel to the suspension of the fluorinating reagent over 1 h while the internal temperature was maintained around −95° C. The funnel and the flask were flushed with 2.5 mL of THF into the reaction mixture. The resulting mixture was stirred at −96° C. for 1 h before warmed to −80° C. over 30 min. Acetic acid (11 mL) in THF (5 mL) was added slowly over 7 min. The mixture was allowed to warm to ambient temperature after the addition of MTBE (100 mL). The resulting solid was removed by filtration and washed thoroughly with MTBE (70 mL×6). The combined filtrate and wash were filtered again and analyzed by HPLC. The chemical yield was determined to be 86%. The filtrate was passed through a short plug of silica gel (30 g), and the plug was washed with MTBE (200 mL). The combined MTBE solutions were concentrated under reduced pressure. The residue was dissolved in EtOAc (250 mL) and washed with saturated aqueous $NaHCO_3$ (170 mL). The aqueous layer was back-extracted with EtOAc (60 mL×2). The combined organic solutions were washed with brine (60 mL) and dried over $Na_2SO_4$. Evaporation of solvent gave the crude ester, which was subjected to bulb-to-bulb distillation (1.6 Torr) to afford the ester as yellow oil. Analytically pure sample was obtained by further flash silica gel column chromatography as colorless oil. $^1$H NMR (400 MHz, $CDCl_3$): δ 5.84 (m, 1H), 5.55 (m, 1H), 4.95 (dd, J=48.8, 5.5 Hz, 1H), 4.49 (dt, J=7.2, 4.6 Hz, 1H), 3.82 (s, 3H), 3.11 (dm, J=24.4 Hz, 1H), 2.75 (m, 1H), 2.51 (s, 1H), 2.33 (m, 1H); $^{13}$C NMR (101 MHz, $CDCl_3$): δ 170.02 (d, J=24.1 Hz), 132.27, 126.13 (d, J=5.0 Hz), 89.52 (d, J=188.0 Hz), 73.92 (d, J=4.0 Hz), 57.12 (d, J=20.1 Hz), 52.64, 41.85; $^{19}$F NMR (376 MHz, $CDCl_3$): −196.5; IR (film) 3409, 3059, 1744, 1439, 1288, 1209, 1153, 1099, 1048, 951, 733 cm$^{-1}$; $[α]_D^{25}$=−123.5 (c 1.02, $CHCl_3$).

Example 2

Methyl fluoro[(1R,2S,3R,5S)-3-hydroxy-6-oxabicyclo[3.1.0]hex-2-yl]acetate 3

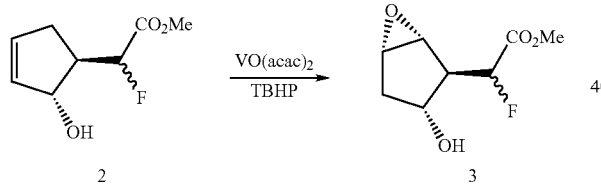

To a solution of olefin 2 (1.92 kg, 11.0 mol) in toluene (4.83 L) was added vanadyl acetylacetonate (VO(acac)$_2$, 58.3 g, 0.22 mol) at 0° C. After a solution of TBHP (5.7 M in decane, 38.6 mL) was added to the solution at 0° C., the resulting suspension was allowed to warm to 14° C. Additional solution of TBHP (5.7 M in decane, 4.36 L) was slowly added to the reaction mixture over 50 min while maintaining the batch temperature between 14-28° C. The resulting suspension was stirred for another 2 h, and then heated at 40° C. for 8 h. Excess TBHP was quenched with aqueous $Na_2S_2O_3$ solution (2.95 kg $Na_2S_2O_3$ and 4.71 kg $H_2O$), which was slowly added at 0° C. The resulting mixture was stirred at 20° C. for 1.5 h. The disappearance of peroxides was confirmed by test paper. The aqueous layer was separated and extracted with EtOAc (9.42 L×2). The combined organic solutions were washed with brine (6.33 L). The brine layer was back-extracted with EtOAc (3.42 L×4). GC assay of the combined organic solutions indicated product 3. The combined organic solutions were concentrated, and the resulting residue was purified by silica gel chromatography in a filter pot (first eluted with hexanes/EtOAc (4/1) then pure EtOAc). Analytically pure sample was prepared by flash silica gel column chromatography (hexanes/MTBE) followed by recrystallization (EtOAc) as pale yellow crystals: mp 31-33° C.; $^1$H NMR (400 MHz, $CDCl_3$) δ 5.01 (dd, J=48.3, 3.9 Hz, 1H), 4.13 (br s, 1H), 3.86 (s, 3H), 3.71 (m, 1H), 3.59 (m, 1H), 2.77 (dd, J=32.8, 3.9 Hz, 1H), 2.30 (br s, 1H), 2.11 (m, 2H); $^{13}$C NMR (101 MHz, $CDCl_3$) δ 168.4 (d, J=24.1 Hz), 88.1 (d, J=186.1 Hz), 73.2 (d, J=1.6 Hz), 58.4, 57.1 (d, J=5.6 Hz), 52.8, 51.6 (d, J=19.3 Hz), 37.7 (d, J=1.6 Hz); $^{19}$F NMR (376 MHz, $CDCl_3$) δ −200.8 (dd, J=48.3, 32.8 Hz); LRMS m/z 191 (M+1), 189 (M−1), 172 ([M−$H_2O$]$^+$), 59 ([$COOCH_3$]$^+$, base peak); $[α]_D^{25}$=−56 (c 1.0, $CHCl_3$).

Analysis calculated for $C_8H_{11}FO_4$ C 50.53; H, 5.83; F, 9.99.

Found: C, 50.36; H, 5.92; F, 10.05.

Example 2A

Methyl[1R,2S,3R,5S)-3-hydroxy-6-oxabicyclo[3.1.0]hex-2-yl]acetate

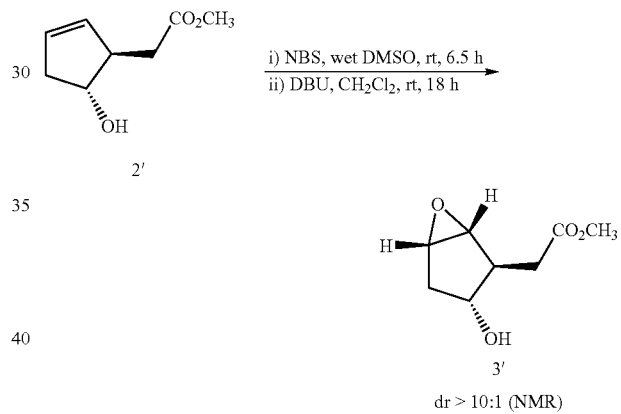

To a solution of olefin 2' (50.0 mg, 0.320 mmol) in wet DMSO (6.4 μL $H_2O$ in 1.2 mL DMSO) at rt was added NBS (68.4 mg, 0.384 mmol). After the resulting solution was stirred at rt for 4.5 h, another 10 mg of NBS was added. The reaction was further stirred at rt for 2 h, diluted with EtOAc, and washed with $H_2O$. The aqueous layer was extracted with EtOAc (twice), and the combined organic layer was dried over $Na_2SO_4$. The solvent was removed under reduced pressure, and the resulting residue was taken in $CH_2Cl_2$ (1.2 mL). DBU (57.4 μL, 0.384 mmol) was added to the solution, which was stirred at rt for 18 h. The solvent was evaporated, and the resulting residue was purified by flash silica gel column chromatography to afford epoxide 3' as a mixture of diastereomers, which were inseparable by chromatography. The spectral data for the major isomer are as follows: $^1$H NMR ($CDCl_3$, 400 MHz) δ 3.80 (dd, J=11.6, 5.6 Hz, 1H), 3.72 (s, 3H), 3.65 (m, 1H), 3.61 (m, 1H), 2.68 (dd, J=8.4, 7.2 Hz, 1H), 2.36 (d, J=11.6 Hz, 1H), 2.26 (dd, J=15.7, 7.2 Hz, 1H), 2.20 (dd, J=15.7, 8.4 Hz, 1H), 2.11 (d, J=15.3 Hz, 1H), 2.02 (dd, J=15.3, 5.6 Hz, 1H).

Under similar reaction conditions, the following epoxides were also prepared:

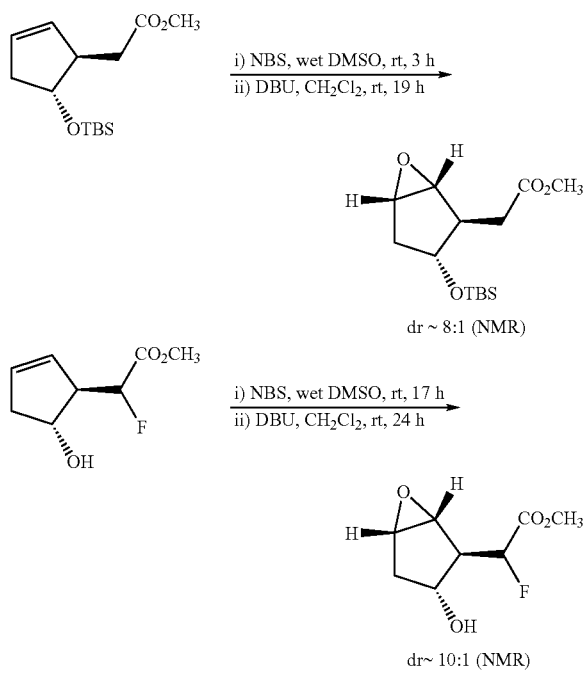

dr ~ 8:1 (NMR)

dr~ 10:1 (NMR)

Example 3

Methyl((1R,2R,3R,5S)-3-{[tert-butyl(dimethyl)silyl]oxy}-6-oxabicyclo[3.1.0]hex-2-yl)fluoroacetate 4

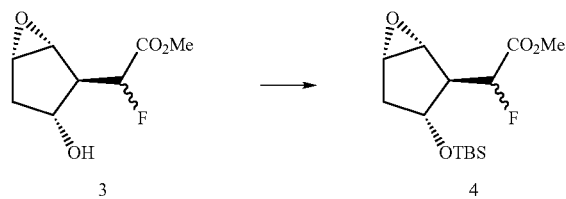

To a solution of epoxy alcohol 3 (1.60 kg, 8.40 mol) and DMF (3.40 L) was added imidazole (1.26 kg, 18.5 mol) at 10° C. TBSCl (1.52 kg, 10.1 mol) was added to the reaction mixture while maintaining the batch temperature below 8° C. The resulting solution was stirred at 5° C. for 10 min, then allowed to warm to 20° C. over 30 min and stirred for 2 h at the same temperature. The consumption of the starting alcohol was monitored by GC, and the reaction mixture was diluted with cold toluene (17.0 L, 5° C.). The resulting mixture was washed with $H_2O$ (5.67 L), saturated aqueous $NaHCO_3$ (5.67 L), $H_2O$ (5.67 L×2), and brine (5.67 L). Assay of the organic solution indicated 4. Concentration of the solution gave 4 as yellow liquid, which was used for the next step without further purification. Analytically pure sample was obtained by flash silica gel column chromatography (hexanes/MTBE) as colorless crystals: mp 28-30° C.; $^1$H NMR (400 MHz, $CDCl_3$) δ 5.00 (dd, J=48.2, 3.5 Hz, 1H), 4.45 (m, 1H), 3.85 (s, 3H), 3.51 (m, 1H), 3.42 (m, 1H), 2.64-2.52 (dm, J=34.5 Hz, 1H), 2.14 (m, 1H), 1.91 (m, 1H), 0.88 (s, 9H), 0.054 (s, 3H), and 0.051 (s, 3H); $^{13}$C NMR (101 MHz, $CDCl_3$) δ 168.8 (d, J=24.1 Hz), 88.3 (d, J=186.1 Hz), 75.4 (d, J=1.6 Hz), 58.3, 57.2 (d, J=7.2 Hz), 52.8 (d, J=19.3 Hz), 52.7, 38.3, 25.9, 18.0, −4.5, and −4.7; $^{19}$F NMR (376 MHz, $CDCl_3$) δ −199.9 (dd, J=48.2, 34.5 Hz); LRMS m/z 305 (M+1), 121 (base peak); $[\alpha]_D^{25}$=−27 (c 1.0, $CHCl_3$).

Analysis calculated for $C_{14}H_{25}FO_4Si$, C, 55.23; H, 8.28; F, 6.24.

Found: C, 55.27; H. 8.63; F, 6.31.

Example 4

Methyl(1R,2R,4S,5S,6R)-2-{[tert-butyl(dimethyl)silyl]oxy}-6-fluoro-4-hydroxybicyclo[3.1.0]hexane-6-carboxylate 5

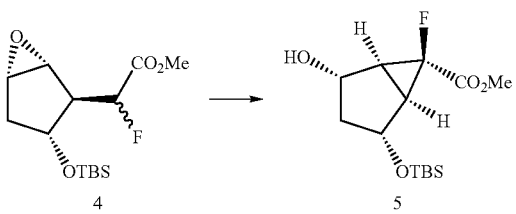

To a solution of epoxide TBS-ether 4 (assay wt. 1.60 kg, 5.24 mol) in THF (16.1 L) was added a solution of $Et_3Al$ (1.0 M in hexanes, 6.81 L, 6.81 mol), while maintaining the batch temperature at −60° C. over 1 h, and the resulting solution was stirred at −60° C. for 20 min. A solution of LHMDS (1.0 M solution in hexanes, 7.86 L, 7.86 mol) was added to the reaction mixture over 1 h while maintaining the batch temperature below −60° C., and the reaction was aged at −60° C. The progress of the reaction was monitored by GC. After complete consumption of the epoxide (6 h), an aqueous solution of citric acid (3 M, 10.5 L) was added over 1 h while maintaining the batch temperature below −50° C. After MTBE (12.4 L) was added, the resulting suspension was gradually allowed to warm to 15° C. with stirring. The mixture turned to biphasic solution after addition of $H_2O$ (4.93 L). The organic layer was separated and washed twice with saturated aqueous $NaHCO_3$ (11.1 L then 5.6 L). GC assay of the organic solution indicated compound 5. Concentration of the organic layer afforded crude alcohol as yellow oil which was used for the next reaction without further purification.

Analytically pure sample was obtained by flash silica gel column chromatography as colorless amorphous solid: $^1$H NMR (400 MHz, $CDCl_3$) δ 4.47 (d, J=4.4 Hz, 1H), 4.34 (m, 1H), 3.83 (s, 3H), 2.44 (d, J=6.8 Hz, 1H), 2.37 (d, J=11.2 Hz, 1H), 2.25 (d, J=6.8 Hz, 1H), 2.07 (m, 1H), 1.84 (m, 1H), 0.91 (s, 9H), 0.131 (s, 3H), and 0.128 (s, 3H); $^{13}$C NMR (101 MHz, $CDCl_3$) δ 169.2 (d, J=26.5 Hz), 79.7 (d, J=244.3 Hz), 74.1, 74.0, 52.9, 44.6 (d, J=10.4 Hz), 37.9 (d, J=12.0 Hz), 37.6 (d, J=11.2 Hz), 25.8, 18.0, −4.8, −4.9; $^{19}$F NMR (376 MHz, $CDCl_3$) δ −217.1 (m); LRMS m/z 305 (M+1), 304 (M), 303 (M−1), 75 (base peak); $[\alpha]_D^{25}$=+7 (c 1.1, $CHCl_3$).

Analysis calculated for $C_{14}H_{25}FO_4Si$ C, 55.23; H, 8.28, F, 6.24.

Found: C, 55.44; H, 8.46; F, 6.39.

Example 5

Methyl(1R,2R,5S,6S)-2-{[tert-butyl(dimethyl)silyl]oxy}-6-fluoro-4-oxobicyclo[3.1.0]hexane-6-carboxylate 6

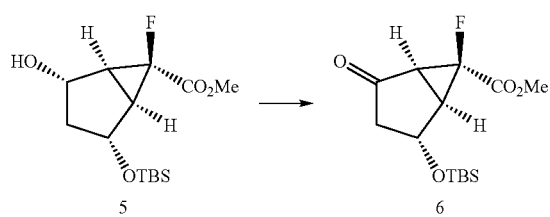

To a solution of bicyclic mono-TBS-diol 5 (2.08 kg; 6.83 mol) in acetonitrile (8.0 L) at −5° C. was added acetic acid (0.70 L) and water (2.5 L), followed by RuCl$_3$ hydrate (14.20 g). To the mixture was added aqueous sodium hypochlorite solution (~13%; 7.0 L) over 2 h, keeping the temperature around 0° C. The resulting mixture was stirred at 0° C. for another 1 h until all bicyclic mono-TBS-diol 5 disappeared, monitoring by TLC and NMR. The excess aqueous sodium hypochlorite was decomposed by the addition of isopropanol (0.70 L), aged at 0° C. for 15 min. The two layers were cut and the aqueous layer was discarded. The solution was used for the next reaction without further treatment. Analytical pure sample was obtained by flash silica gel column chromatography (MTBE/hexane) as colorless crystals: mp 70-71° C.; $^1$H NMR (400 MHz, CDCl$_3$): δ 4.66 (d, J=5.4 Hz, 1H), 3.86 (s, 3H), 3.73 (s, 3H), 2.73 (m, 2H), 2.54 (dt, J=19.1, 5.7 Hz, 1H), 2.22 (dd, J=19.1, 3.8 Hz, 1H), 0.91 (s, 9H), 0.13 (s, 3H), 0.11 (s, 3H); $^{13}$C NMR (101 MHz, CDCl$_3$): δ 206.2, 167.1 (d, J=26.1 Hz), 78.9 (d, J=246.4 Hz), 67.6 (d, J=2.8 Hz), 53.4, 47.5 (d, J=3.9 Hz), 42.0 (d, J=11.4 Hz), 39.6 (d, J=13.3 Hz), 25.7, 18.0, −4.76, and −4.78; $^{19}$F NMR (376 MHz, CDCl$_3$): δ −210.7; $[\alpha]_D^{25}$=+58.2 (c 0.50, CH$_3$OH).

Analysis calculated for C$_{14}$H$_{23}$FO$_4$Si C, 55.60; H, 7.67, F, 6.28.

Found: C, 55.60; H, 7.56; F, 6.33.

Example 6

Methyl(1R,2R,5S,6S)-6-fluoro-2-hydroxy-4-oxobicyclo[3.1.0]hexane-6-carboxylate 7

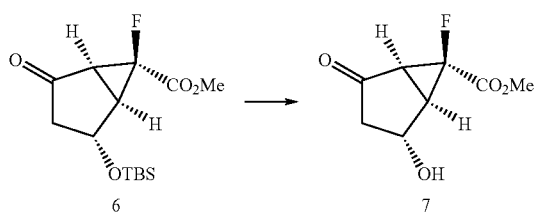

The above organic layer, containing TBS-ketone 6 (6.83 mol) was warmed to 22° C. and 1 M HCl (1.37 L) was added. The mixture was stirred at 22-24° C. for 3.5 h until all TBS groups were removed. To the mixture was added saturated sodium bicarbonate solution (4.8 L). The mixture was stirred for 15 min, diluted with isopropyl acetate (20 L), and the organic layer was separated. The aqueous layer was back extracted with isopropyl acetate (6 L). The combined organic solutions were concentrated to dryness and the compound was purified by silica gel chromatography in a filter pot (first eluted with 30% MTBE in hexane, then MTBE alone) to give compound 7 as an off white crystal. Analytical pure sample was obtained by further flash silica gel column as colorless crystals: mp 61-62° C.; $^1$H NMR (400 MHz, CDCl$_3$): δ 4.92 (br s, 1H), 3.85 (s, 3H); 2.86 (dd, J=6.2, 2.1 Hz, 1H), 2.71 (d, J=6.2 Hz, 1H), 2.61 (dt, J=19.4, 5.7 Hz, 1H), 2.59 (br s, 1H), 2.30 (dd, J=19.4, 3.7 Hz, 1H); $^{13}$C NMR (100 MHz, CDCl$_3$): δ 206.9, 167.0 (d, J=26.2 Hz), 79.0 (d, J=246.6 Hz), 67.0 (d, J=3.1 Hz), 53.5, 46.8 (d, J=4.2 Hz), 41.6 (d, J=11.8 Hz), 39.4 (d, J=13.1 Hz); $^{19}$F NMR (376 MHz, CDCl$_3$): δ −210.6; $[\alpha]_D^{25}$=+77 (c 0.50, CH$_3$OH).

Analysis calculated for C$_8$H$_9$FO$_4$ C, 51.07; H, 4.82, F, 10.10.

Found: C, 51.06; H, 4.83; F, 10.05.

Example 6A

Methyl(1S,2R,5R,6R)-2-hydroxy-4-oxobicyclo[3.1.0]hexane-6-carboxylate

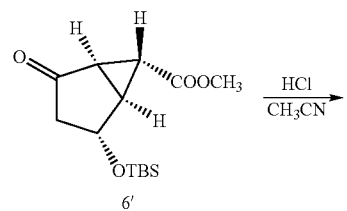

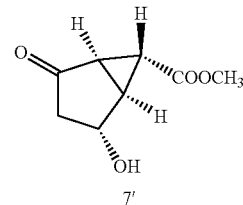

TBS-ether 6' (150 mg, 0.528 mmol) was treated with 1 M HCl (0.106 mL) in acetonitrile (0.8 mL) at rt for 2 h. The reaction was diluted with EtOAc, quenched by addition of a small amount of saturated aq. NaHCO$_3$, washed with H$_2$O and brine (twice), and dried over Na$_2$SO$_4$. The solvents were removed under reduced pressure, and the resulting residue was purified by flash silica gel column chromatography to afford hydroxy ketone 7' as colorless solid: $^1$H NMR (CDCl$_3$, 400 MHz) δ 4.60 (d, J=5.2 Hz, 1H), 3.72 (s, 3H), 2.67 (dd, J=5.2, 3.6 Hz, 1H), 2.42 (dd, J=5.2, 2.4 Hz, 1H), 2.34 (dd, J=18.9, 5.2 Hz, 1H), 2.22 (br-s, 1H), 2.08 (d, J=18.9 Hz, 1H), 1.93 (dd, J=3.6, 2.4 Hz, 1H); $^{13}$C NMR (CDCl$_3$, 101 MHz) δ 208.8, 169.8, 68.3, 52.5, 42.7, 36.2, 34.2, 25.2.

Example 7

Methyl(1S,4R,4'S,5R,5'S,6S)-6-fluoro-4-hydroxy-4',5'-diphenylspiro[bicyclo[3.1.0]hexane-2,2'-[1.3]dioxolane]6-carboxylate 8

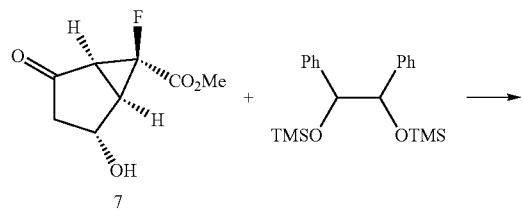

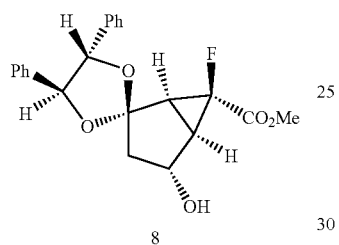

Example 8

Methyl(1S,4'S,5R,5'S,6S)-6-fluoro-4-oxo4',5'-diphenylspiro[bicyclo[3.1.0]hexane-2,2'-[1.3]dioxolane]-6-carboxlate 9

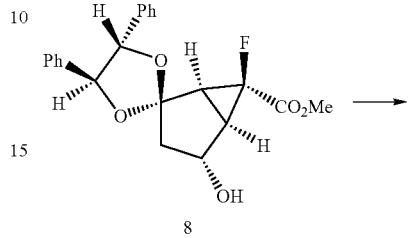

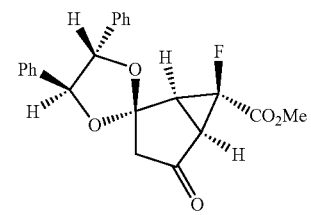

To a solution of hydroxy ketone 7 (1.09 kg; 5.76 mol) and $CH_2Cl_2$ (7.7 L) was added a solution of (S,S)-bis-O-TMS-hydrobenzoin (assay 2.01 kg; 5.60 mol) and $CH_2Cl_2$ (2.55 L). The solution was cooled to −20° C. TfOH (50.9 mL; 0.576 mol) was charged through an addition funnel over 4 min at −15~−20° C. The solution was warmed to −10° C. and aged at −10° C. for 1.5 h. An additional solution of (S,S)-bis-O-TMS-hydrobenzoin (assay 107 g; 0.298 mol) in $CH_2Cl_2$ (188 g) was charged to the reaction mixture at −10° C. The reaction was completed after 30 min additional age at −10° C. The reaction was quenched by addition of pyridine (46.9 mL; 0.576 mol) at <−15° C. The solution was warmed to −10° C., washed with 5 wt % of cold aqueous solution of $NaHCO_3$ (3.75 L), 1 M cold aqueous HCl (8.6 L), 5 wt % cold aqueous $NaHCO_3$ (3.75 L), and 10 wt % cold aqueous NaCl (5.0 L) in turn, dried over $Na_2SO_4$ (1.5 kg). The solvent of the organic solution was switched into acetonitrile and used for the next reaction without further purification. HPLC assay of the solution at this point indicated the ketal alcohol 8. Analytically pure sample was obtained by flash silica gel column chromatography as colorless crystals: mp 118-120° C.; $^1$H NMR (401 MHz, $CDCl_3$): δ 7.38-7.21 (m, 10H), 4.89 (d, J=8.3 Hz, 1H), 4.83 (d, J=8.3 Hz, 1H), 4.51 (br s, 1H), 3.89 (s, 3H), 2.54-2.51 (m, 2H), 2.43-2.37 (m, 2H), 2.18 (br s, 1H); $^{13}$C NMR (101 MHz, $CDCl_3$): δ 168.7 (d, J=25.7 Hz), 136.6, 135.8, 128.7, 128.6, 128.5, 128.4, 126.9, 126.3, 117.7, 86.2, 86.1, 77.6 (d, J=247.1 Hz), 71.1, 53.0, 45.7 (d, J=7.8 Hz), 37.5 (d, J=12.1 Hz), 36.7 (d, J=11.9 Hz); $^{19}$F NMR (377 MHz, $CDCl_3$): δ −216.3.

To a solution of hydroxy ketal 8 (assay 2.04 kg, 5.31 mol) in acetonitrile (36.7 L) was added $RuCl_3$ hydrate (8.25 g) followed by water (2.0 L) and acetic acid (0.41 L) at 0° C. Aqueous sodium hypochloride solution (~13%, 5.37 L) was added to the reaction solution slowly over 19 min, while maintaining the reaction temperature below 4° C. The solution was aged at 0-3.5° C. for 2 h. The reaction was quenched by addition of isopropanol (2.2 L) at 3.5° C. After 30 min aging at the same temperature, aqueous cold $NaHCO_3$ (5 wt %, 10.7 L) was added to the mixture over 12 min between 0.4 and 3.3° C. The resulting slurry was stirred for 30 min at 3° C., and the product 9 was filtered. The wet cake was washed with cold water (2 L×2) and dried to give the first crop of the ketal ketone 9. The filtrate and washes were combined and the layers were separated. The organic layer was concentrated in vacuo. The resulting slurry was filtered. The cake was washed with water (0.48 L×2) and was recrystallized from acetonitrile (1.8 L) and water (1.08 L) to give the second crop of ketal ketone 9. Analytically pure sample was obtained by flask silica gel column chromatography as colorless crystals: mp 58.5-59.5° C.; $^1$H NMR (400 MHz, $CDCl_3$): δ 7.40-7.34 (m, 6H), 7.28-7.25 (m, 4H), 4.97 (d, J=8.4 Hz, 1H), 4.88 (d, J=8.4 Hz, 1H), 3.93 (s, 3H), 3.10 (dd, J=6.4, 2.0 Hz, 1H), 2.94 (d, J=4.0 Hz, 2H), 2.87 (d, J=6.4 Hz, 1H); $^{13}$C NMR (101 MHz, $CDCl_3$): δ 201.5, 166.9 (d, J=25.7 Hz), 136.1, 135.3, 129.0, 128.8, 128.72, 128.69, 126.8, 126.5, 110.8, 86.3, 85.8, 78.9 (d, J=251.6 Hz), 53.6, 48.3 (d, J=3.3 Hz), 42.2 (d, J=13.2 Hz), 41.7 (d, J=12.0 Hz); $^{19}$F NMR (376 MHz, $CDCl_3$): δ −208.5.

Example 9

(1S,4'S,5R,5'S,6S)-4-Amino-4-cyano-6-fluoro-4',5'diphenylspiro[bicyclo[3.1.0]hexane-2,2'-[1,3]dioxolane]-6-carboxamide 10

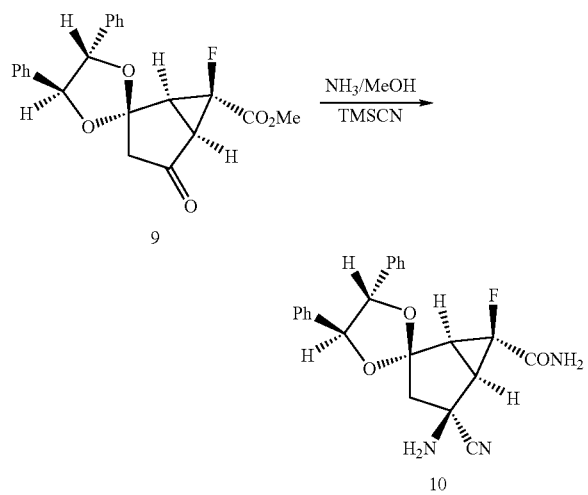

To a solution of 7 M ammonia in methanol (7.4 L, 47.8 mol) and Ti(OiPr)$_4$ (1.77 L, 5.93 mol) at 23° C. was added ketal ketone 9 (2.11 kg, 1.89 kg as pure 9, 4.94 mol). The mixture was stirred for 4 h at 20-23° C. The mixture was cooled to −12° C., and TMSCN (505 g, 5.09 mol) was added. The mixture was warmed to −4.5° C. and stirred at that temperature for 16 h. The mixture was filtered and crystals were washed with cold MeOH (7.0 L), and dried at 20-25° C. at reduced pressure to afford aminonitrile 10 as a colorless solid. Analytically pure sample was prepared by silica gel column chromatography as colorless crystals: mp. 196.9-197.4° C. $^1$H NMR (400 MHz, DMSO-d$_6$): δ 8.04 (s, 1H), 7.78 (s, 1H), 7.38-7.25 (m, 10H), 5.15 (d, J=8.8 Hz, 1H), 4.81 (d, J=8.8 Hz, 1H), 2.86, (s, 2H), 2.78 (dd, J=14.5, 3.2 Hz, 1H), 2.63 (d, J=6.8 Hz, 1H), 2.46 (d, J=6.8 Hz, 1H), and 2.23 (dd, J=14.5, 4.4 Hz, 1H). $^{13}$C NMR (101 MHz, DMSO-d$_6$): δ 168.7 (d, J=23.3 Hz), 136.5, 135.9, 128.6, 128.5, 128.5, 127.1, 126.9, 123.4, 115.1, 84.7, 84.3, 81.1 (d, J=255.4 Hz), 54.6, 48.3 (d, J=7.2 Hz), 36.6 (d, J=11.2 Hz), and 35.9 (d, J=10.4 Hz). $^{19}$F NMR (377 MHz, DMSO-d$_6$): δ −211.6.

Example 10

(1R,2S,5S,6S)-2-Amino-6-fluoro-4-oxobicyclo[3.10]hexane-2,6-dicarboxylic acid 11

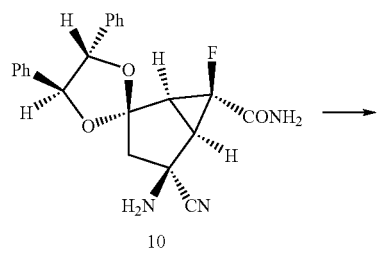

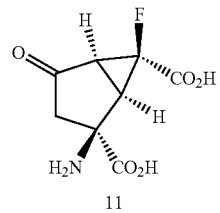

A mixture of aminonitrile 10 (1.63 kg crude, 1.55 kg pure basis), HOAc (3.25 L), H$_2$O (3.25 L), and conc. HCl (6.50 L) was heated to 75±2° C. for 4 h. $^{19}$F NMR showed that the reaction was complete. The solution was cooled to 18° C. and extracted with CH$_2$Cl$_2$ (1×9 L and 2×5 L). The aqueous layer was concentrated at 10-25 torr and 50° C. internal temperature to ~2 L. The resulting slurry was cooled to 0° C. and stirred for 1 h. The cooled slurry was filtered, and the cake containing HCl salt of product 11 was maintained under vacuum filtration for 5-10 min to remove as much of the filtrate as possible. The cake of HCl salt from above was added to water (5.0 L) at 65° C., and rinsed in with hot H$_2$O (300 mL). The solution was allowed to cool to 17° C. over 45 min. The pH was adjusted to 1.25 with 50% NaOH (230 mL). The slurry was cooled to 0° C. and stirred for 45 min. The slurry was filtered, washed with H$_2$O (2×1 L), and dried under nitrogen to afford the off-white crystalline product 11 as monohydrate. Analytically pure HCl salt of 11 was obtained from 20% HCl: mp. 195-220 (decomp); $^1$H NMR (401 MHz, DMSO-d$_6$): δ 8.99 (s, 2H), 3.08 (dd, J=6.4, 1.6 Hz, 1H), 3.02 (d, J=6.4 Hz, 1H), 2.86 (dd, J=18.5, 3.6 Hz, 1H), 2.57 (dd, J=18.5, 4.8 Hz, 1H); $^{13}$C NMR (101 MHz, DMSO-d$_6$): δ 201.3 (d, J=2.7 Hz), 170.4, 166.3 (d, J=25.7 Hz), 78.9 (d, J=247.0 Hz), 58.1 (d, J=1.5 Hz), 40.6 (d, J=13.1 Hz), 36.8 (d, J=11.1 Hz); $^{19}$F NMR (377 MHz, DMSO-d$_6$): δ −204.8; Cl Titration 13.96% (Theory 13.98%).

Example 11

Methyl((1R,2R,3R,5S)-3-{[tert-butyl(dimethyl)silyl]oxy}-6-oxabicyclo[3.1.0]hex-2-yl)acetate

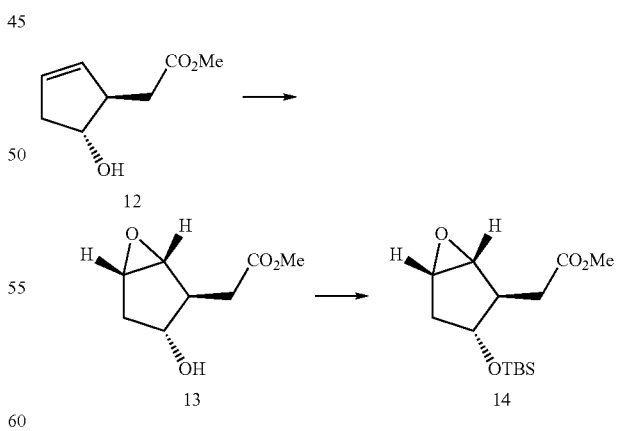

To a solution of olefin 12 (4.25 g, 27.2 mmol) in toluene (10.8 mL), was added vanadyl acetylacetonate (VO(acac)$_2$, 289 mg, 1.09 mmol, 4 mol %). A solution of TBHP (14.3 mL, 81.6 mmol, 5.7 M in decane) was added over 30 min while maintaining the internal temperature below 28° C. The resulting mixture was stirred at rt for 5.5 h and quenched by addition of saturated aq. Na$_2$S$_2$O$_3$. The aqueous layer was separated and extracted by ethyl acetate (×5). The combined organic layers were washed with brine and dried over Na$_2$SO$_4$. Solvents were evaporated, and the resulting residue was purified by flash silica gel chromatography to afford epoxy alcohol 13 as colorless liquid, which contained inseparable byproducts. This alcohol (3.21 g) was treated with imidazole (2.78 g, 40.9 mmol) and TBSCl (3.36 g, 22.3 mmol) in DMF (7.2 mL) at ambient temperature to convert the hydroxyl group to the TBS-ether. The reaction mixture was stirred at rt for 2.5 h and then treated with MTBE (36 mL) and H$_2$O (12 mL). The organic layer was separated, washed with saturated aq. NaHCO$_3$, H$_2$O and brine, and dried over Na$_2$SO$_4$. Solvent was evaporated, and the resulting residue was purified by flash silica gel chromatography to afford TBS-ether 14 as a colorless liquid: $^1$H NMR (CDCl$_3$, 400 MHz) δ 4.08 (m, 1H), 3.72 (s, 3H), 3.49 (m, 1H), 3.37 (m, 1H), 2.49 (m, 1H), 2.31 (d, J=7.2 Hz, 1H), 2.31 (m, 1H), 2.09 (A, 1H), 1.93 (m, 1H), 0.88 (s, 9H) 0.04 (s, 3H), 0.03 (s, 3H); $^{13}$C NMR (CDCl$_3$, 101 MHz) δ 171.9, 77.0, 60.4, 57.4, 51.7, 46.4, 37.2, 34.6, 25.8, 18.0, −4.7; LRMS m/z 287 (M+1), 286 (M), 285 (M−1), 169 (base peak);

Analysis calculated for C$_{14}$H$_{26}$O$_4$Si C, 58.70; H, 9.15. Found C, 58.45; H, 9.49.

Example 12

Methyl(1S,2R,4S,5R,6S)-2-{[tert-butyl(dimethyl) silyl]oxy}4-hydroxybicyclo[3.1.0]hexane-6-carboxylate

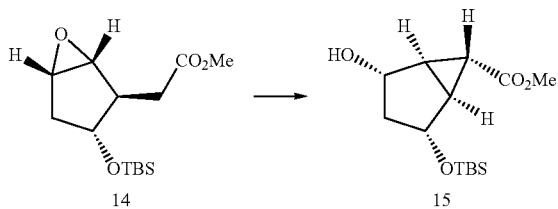

14    15

To a solution of epoxide 14 (3.52 g, 12.3 mmol) in THF (37.8 mL) at −70° C., was added a solution of Et$_3$Al (16.0 mL, 16.0 mmol, 1 M in hexanes). After the resulting solution was stirred at −70° C. for 10 min, a solution of LHMDS (18.4 mL, 18.4 mmol, 1 M in hexanes) was added slowly over 30 min. The resulting solution was stirred at −70° C. for 100 min and quenched by addition of aq. citric acid (24.9 mL, 3 M). After toluene (24.9 mL) was added, the resulting mixture was allowed to warm to ambient temperature, and H$_2$O (11.7 mL) was added. The aqueous layer was separated and extracted with MTBE (20 mL). The combined organic layers were washed with saturated aq. NaHCO$_3$ (36 mL×2) and brine and dried over Na$_2$SO$_4$. Solvent was evaporated, and the resulting residue was purified by flash silica gel column chromatography to afford bicyclic alcohol 15 as colorless oil: $^1$H NMR (CDCl$_3$, 400 MHz) δ 4.34 (d, J=4.4 Hz, 1H), 4.18 (dd, J=11.6, 4.4 Hz, 1H), 3.68 (s, 3H), 2.46 (d, J=11.6 Hz, 1H), 2.26 (dd, J=6.0, 2.8 Hz, 1H), 2.10 (dd, J=6.0, 2.8 Hz, 1H), 1.67 (d, J=15.3 Hz, 1H), 1.49 (dt, J=15.3, 4.4 Hz, 1H), 1.16 (t, J=2.8 Hz, 1H), 0.90 (s, 9H), 0.13 (s, 3H), 0.11 (s, 3H); $^{13}$C NMR (CDCl$_3$, 101 MHz) δ 172.2, 73.8, 73.6, 51.9, 40.3, 33.3, 33.0, 25.7, 21.8, 17.9, −4.8, −5.0; LRMS m/z 287 (M+1), 286 (M), 285 (M−1), 169 (base peak);

Analysis calculated for C$_{14}$H$_{26}$O$_4$Si C, 58.70; H, 9.15. Found C, 58.55; H, 9.34.

Example 13

Methyl(1S,2R,4S,5R,6R)-2-{[tert-butyl(dimethyl) silyl]oxy}-4-{[(4-methylphenyl)sulfonyl] oxy}bicyclo[3.1.0]hexane-6-carboxylate

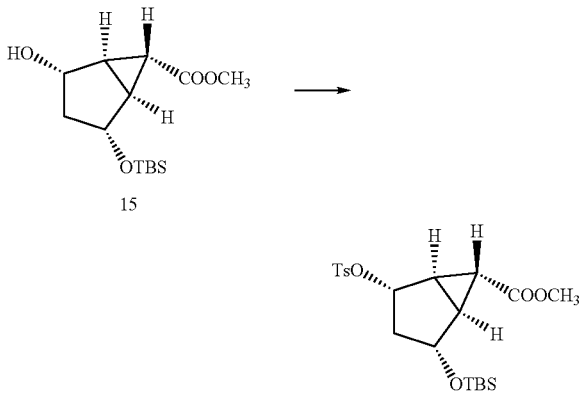

15

16

To a stirred solution of alcohol 15 (929 mg, 3.24 mmol) in CH$_2$Cl$_2$ (3.8 mL) at 0° C., were added pyridine (2.62 mL, 32.4 mmol) and p-toluenesulfonyl chloride (1.24 g, 6.49 mmol). The resulting mixture was allowed to warm to ambient temperature and stirred at the same temperature for 15 h. Saturated aq. NaHCO$_3$ (5 mL) was added to the reaction mixture, and the resulting mixture was stirred at room temperature for 1 h. The aqueous layer was separated and extracted with MTBE (10 mL×2). The combined organic layer was washed with 1 M HCl (40 mL), saturated aq. NaHCO$_3$ (10 mL) and brine (10 mL) and dried over Na$_2$SO$_4$. Solvent was evaporated, and the resulting residue was purified by flash silica gel chromatography to afford p-toluenesulfonate ester 16 as colorless solid: $^1$H NMR (CDCl$_3$, 400 MHz) δ 7.81 (d, J=8.0 Hz, 2H), 7.33 (d, J=8.0 Hz, 2H), 5.02 (d, J=5.2 Hz, 1H), 4.27 (d, J=4.8 Hz, 1H), 3.65 (s, 3H), 2.45 (s, 3H), 2.30 (dd, J=5.6, 2.8 Hz, 1H), 2.15 (dd, J=5.6, 3.2 Hz, 1H), 1.85 (d, J=16.5 Hz, 1H), 1.64 (ddd, J=16.5, 5.2, 4.8 Hz, 1H), 1.06 (dd, J=3.2, 2.8 Hz, 1H), 0.86 (s, 9H), 0.07 (s, 3H), 0.04 (s, 3H); $^{13}$C NMR (CDCl$_3$, 101 MHz) δ 171.4, 144.5, 134.5, 129.7, 127.6, 82.4, 72.7, 52.0, 40.0, 34.8, 31.3, 25.7, 21.6, 21.1, 17.9, −4.7, −4

Example 14

Methyl(1S,2R,4S,5R,6R)-2-hydroxy-4-{[(4-methylphenyl)sulfonyl]oxy}bicyclo[3.1.0]hexane-6-carboxylate

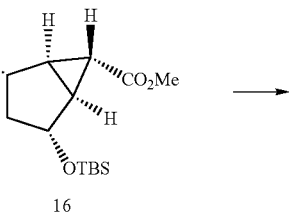

16

-continued

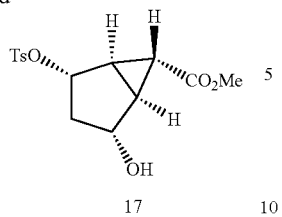

17

TBS-ether 16 (1.86 g, 4.22 mmol) was treated with 0.84 mL of aq HCl (1 M) in acetonitrile (9.4 mL) at rt for 4 h. The reaction was quenched by addition of saturated aq. NaHCO$_3$ (8.7 mL) and MTBE (20 mL). The aqueous layer was separated and extracted with MTBE (10 mL×2). The combined organic layer was dried over Na$_2$SO$_4$ and concentrated under reduced pressure. Treatment of the resulting residue with hexanes gave crystals, which were filtered and recrystallized from hexanes/EtOAc to afford pure alcohol 17 as colorless crystals: $^1$H NMR (CDCl$_3$, 400 MHz) δ 7.82 (d, J=8.0 Hz, 2H), 7.38 (d, J=8.0 Hz, 2H), 5.01 (d, J=5.2 Hz, 1H), 4.24 (d, J=5.2 Hz, 1H), 3.67 (s, 3H), 2.47 (s, 3H), 2.33-2.28 (m, 2H), 1.93 (d, J=16.5 Hz, 1H), 1.67 (dt, J=16.5, 5.2 Hz, 1H), 1.16 (t, J=3.0 Hz, 1H); $^{13}$C NMR (CDCl$_3$, 101 MHz) δ 171.1, 145.1, 133.9, 130.1, 127.8, 83.2, 72.7, 52.2, 39.3, 33.9, 30.8, 21.8, 21.7.

Example 15

Methyl(1R,5S,6S)-4-oxobicyclo[3.1.0]hex-2-ene-6-carboxylate

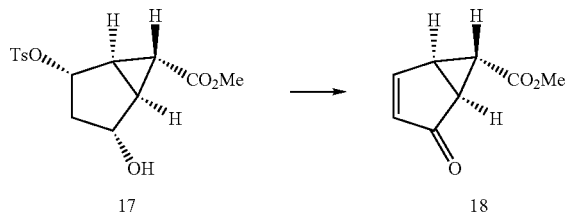

To a solution of DMSO (0.404 mL, 5.70 mmol) in CH$_2$Cl$_2$ (2.6 mL), was added a solution of trifluoroacetic anhydride (0.604 mL, 4.28 mmol) in CH$_2$Cl$_2$ (1.5 mL) at −78° C. The resulting solution was stirred at −78° C. for 30 min, and a solution of alcohol 17 (0.885 g, 2.85 mmol) in CH$_2$Cl$_2$ (4.1 mL) was added (flask was rinsed with 1.0 mL CH$_2$Cl$_2$). After the resulting solution was stirred at −78° C. for 30 min, Et$_3$N (1.59 mL, 11.4 mmol) was slowly added. The resulting mixture was stirred at −78° C. for 2.5 h, and the reaction was quenched by addition of H$_2$O (5 mL). After MTBE (10 mL) was added, the resulting mixture was allowed to warm to rt, and the aqueous layer was separated and extracted with MTBE (10 mL). The combined organic layer was washed with 1 M HCl (15 mL), saturated aq NaHCO$_3$ (10 mL), H$_2$O (10 mL) and brine (10 mL) and dried over Na$_2$SO$_4$. The solvent was evaporated, and the resulting residue was purified by flash silica gel column chromatography to afford α,β-unsaturated ketone 18 as pale yellow crystals: $^1$H NMR (CDCl$_3$, 400 MHz) δ 7.61 (ddd, J=5.6, 2.4, 0.8 Hz, 1H), 5.74 (d, J=5.6 Hz, 1H), 3.71 (s, 3H), 2.96 (m, 1H), 2.62 (m, 1H), 2.27 (m, 1H); $^{13}$C NMR (CDCl$_3$, 101 MHz) δ 203.1, 168.4, 159.5, 129.7, 52.3, 45.4, 30.0, 28.9.

Example 16

Methyl(1S,2R,5R,6R)-2-{[tert-butyl(dimethyl)silyl]oxy}-4-oxobicyclo[3.1.0]hexane-carboxylate (21)

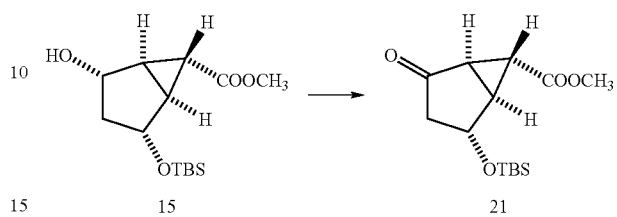

To a solution of DMSO (0.358 mL, 5.04 mmol) in CH$_2$Cl$_2$ (2.5 mL) was added dropwise a solution of trifluoroacetic anhydride (0.534 mL, 3.78 mmol) in CH$_2$Cl$_2$ (1.3 mL), while maintaining the reaction temperature below −70° C. The resulting solution was stirred at −78° C. for 55 min. A solution of alcohol 15 (722 mg, 2.52 mmol) in CH$_2$Cl$_2$ (3.7 mL+1.0 mL rinse) was added dropwise, while maintaining the inside temperature below −75° C. After stirring at −78° C. for 30 min, triethylamine (1.05 mL, 7.56 mmol) was added slowly over 15 min, maintaining the reaction temperature below −74.5° C. The resulting mixture was stirred at −78° C. for 30 min and allowed to warm to −20° C. over 20 min. The reaction was further stirred at −20° C. for 30 min and quenched by addition of H$_2$O. The organic layer was separated, diluted with GIBE, washed with 0.5 M HCl, H$_2$O, saturated aq. NaHCO$_3$, and brine, and dried over Na$_2$SO$_4$. Solvent was removed under reduced pressure, and the resulting residue was purified by flash silica gel column chromatography to afford colorless solid 21 (673 mg, 94% yield): $^1$H NMR (CDCl$_3$, 400 MHz) δ 4.52 (d, J=5.2 Hz, 1H), 3.72 (s, 3H), 2.57 (dd, J=5.2, 3.6 Hz, 1H), 2.40 (m, 1H), 2.28 (dd, J=18.5, 5.2 Hz, 1H), 1.99 (d, J=18.5 Hz, 1H), 1.87 (dd, J=3.6, 2.8 Hz, 1H), 0.89 (s, 9H), 0.11 (s, 3H), 0.09 (s, 3H); $^{13}$C NMR (CDCl$_3$, 101 MHz) δ 209.2, 170.0, 68.8, 52.4, 43.2, 36.8, 34.5, 25.7, 25.0, 18.0, −4.7, −4.8.

Example 17

Methyl(1S,5R,6R)-4-oxobicyclo[3.1.0]hex-2-ene-6-carboxylate (22)

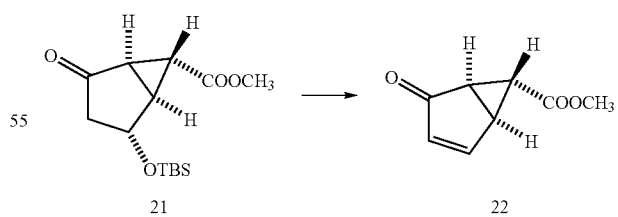

TBS ether 21 (50.0 mg, 0.176 mmol) was treated with DBU (0.0789 mL, 0.528 mmol) in CH$_2$Cl$_2$ (0.9 mL) at rt for 1 h. The reaction was diluted with MTBE, washed with 1 M HCl and brine (twice), and dried over Na$_2$SO$_4$. Solvent was removed under reduced pressure, and the resulting residue was purified by flash silica gel column chromatography to afford colorless solid 22: $[α]_D^{20}$+272.2 (c 1.1, CHCl$_3$). The other spectra were identical to those of the α,β-unsaturated ketone 18 obtained in Example 15.

Characterization of Polymorph of the hydrochloride salt of (1R,2S,5S,6S)-2-Amino-6-fluoro-4-oxobicyclo[3.10]hexane-2,6-dicarboxylic acid 11.

X-ray powder diffraction studies are widely used to elucidate molecular structures, crystallinity and polymorphism. X-ray powder diffraction (XRPD) patterns were collected for the crystal form of a sample of the HCl salt obtained in Example 10, using a Phillips diffractometer. Measurements were made from 3.0080 degrees to 39.9830 degrees (2 theta).

XRPD is depicted at FIG. 1. The following reflections can be used to identify the crystal form:

Scan Parameters

Measurement Date/Time: Jul. 18, 2003 10:6

Raw Data Origin: PHILIPS-binary (scan) (.RD)

Scan Axis: Gonio

Start Position [°2Th.]: 3.0080

End Position [°2Th.]: 39.9830

Step Size [°2Th.]: 0.0170

Scan Step Time [s]: 10.1500

Scan Type: CONTINUOUS

Offset [°2Th.]: 0.0000

Anode Material: Cu

Generator Settings: 40 kV, 50 mA

Spinning: Yes

The peak list for the XRPD is depicted below, in Table 1:

TABLE 1

Peak List

| Pos.[°2Th.] | Heights[cts] | FWHM[°2Th.] | d-spacing[Å] | Rel. Int.[%] |
|---|---|---|---|---|
| 16.5056 | 260.27 | 0.1171 | 5.37086 | 28.52 |
| 19.6239 | 261.89 | 0.1673 | 4.52388 | 28.70 |
| 21.9330 | 189.45 | 0.1338 | 4.05255 | 20.76 |
| 23.1656 | 535.89 | 0.1171 | 3.83964 | 58.72 |
| 26.4349 | 912.56 | 0.1171 | 3.37172 | 100.00 |
| 30.2118 | 242.15 | 0.2007 | 2.95827 | 26.54 |
| 32.8470 | 633.43 | 0.2007 | 2.72671 | 69.41 |
| 33.5963 | 108.10 | 0.2007 | 2.66759 | 11.85 |
| 34.6396 | 70.31 | 0.4015 | 2.58960 | 7.70 |
| 37.2009 | 87.95 | 0.2676 | 2.41698 | 9.64 |

Thus, in one embodiment, the polymorphic form of (1R,2S,5S,6S)-2-Amino-6-fluoro-4-oxobicyclo[3.10]hexane-2,6-dicarboxylic acid HCl has a d-spacing determined by x-ray powder diffraction, CuK alpha, of about 5.37 angstroms. In other embodiments, the polymorphic form of (1R,2S,5S,6S)-2-Amino-6-fluoro-4-oxobicyclo[3.10]hexane-2,6-dicarboxylic acid HCl has at least one d-spacing determined by x-ray powder diffraction, CuK alpha, of about 4.52, 4.05, 3.84, 3.37, 2.96, 2.73, 2.67, 2.59 or 2.42 angstroms.

Figure 2:
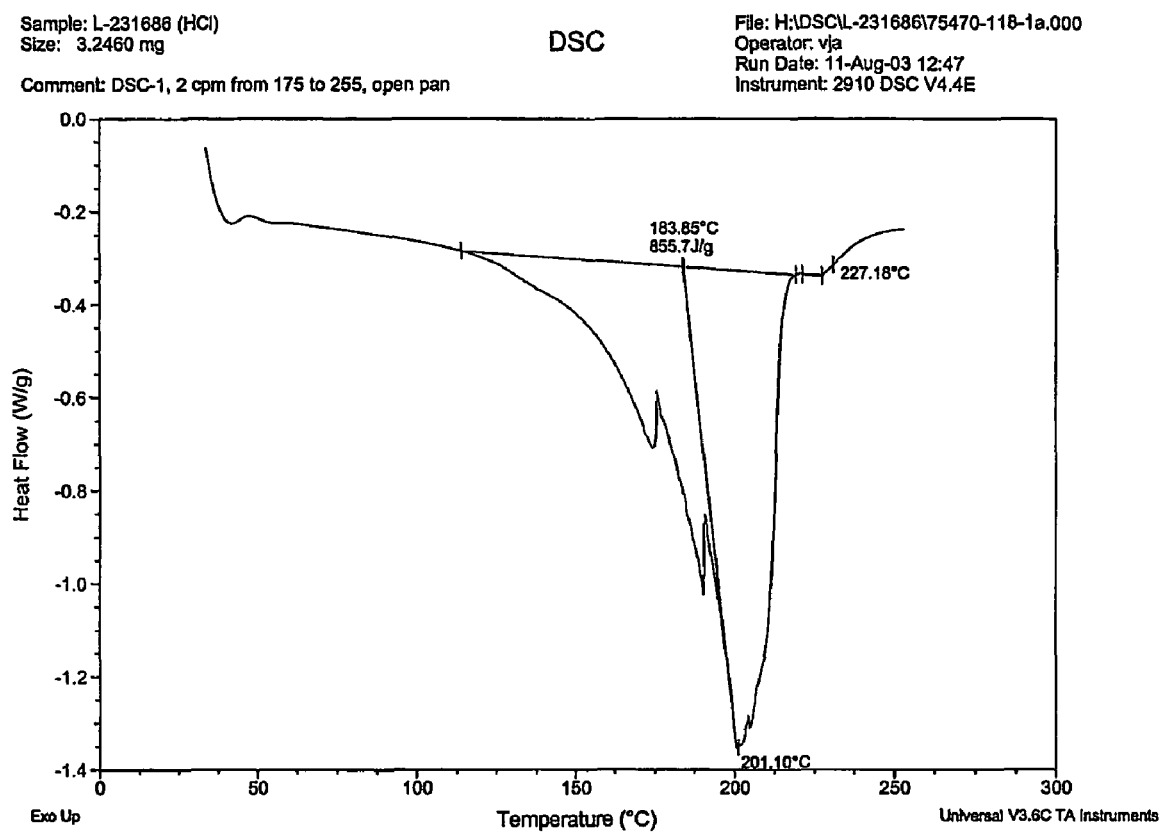
FIG. 2 depicts the differential scanning calorimetry curve for a crystal form of the hydrochloride salt of (+)-(1R,2S,5S, 6S)-2-amino-6-fluoro-4-oxobicyclo[3.1.0]hexane-2,6-dicarboxylic acid.

Differential Scanning Calorimetry (DSC) of the sample of the HCl salt obtained in Example 10 was carried out using a TA Instruments DSC 2910 instrument at a heating rate of 10° C./min from 20° C. to 175° C. and at 2° C./min from 175° C. to 255° C. under a nitrogen atmosphere in an open pan. The results are depicted in FIG. 2. The results showed a broad melting point with an onset temperature of about 184° C. followed by exothermic decomposition above 227° C.

Thus, in one embodiment, the polymorphic form of (1R,2S,5S,6S)-2-Amino-6-fluoro-4-oxobicyclo[3.10]hexane-2,6-dicarboxylic acid HCl has a Differential Scanning Calorimetry extrapolated onset melting temperature of about 184° C.

The following abbreviations are used throughout the text:

Me: methyl

Et: ethyl iPr: isopropyl

Bu: butyl

Ac: acetyl

DBU: 1,8-diazabicyclo[5.4.0]undec-7-ene

NBS: N-bromo succinimide

NIS: N-iodo succinimide

DMF: N,N'-dimethylformamide

THF tetrahydrofuran

TBHP: tertiary butyl hydroperoxide

MTBE: methyl tertiary butyl ether

LDA: lithium diisopropylamide

TBS: tertiary butyldimethylsilyl

TMS: trimethylsilyl

TES: triethylsilyl

DMSO: dimethylsulfoxide

TfOH: trifluoromethanesulfonic acid

LHMDS lithium hexamethyldisilazide

Ts: para-toluenesulfonyl (tosyl)

HPLC: high performance liquid chromatography

GC: gas chromatography

NMR: nuclear magnetic resonance

DSC: differential scanning colorimetry

TLC: thin layer chromatography

XRPD: x-ray powder diffraction rt: room temperature

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, reaction conditions other than the particular conditions as set forth herein above may be applicable as a consequence of variations in the reagents or methodology to prepare the compounds from the processes of the invention indicated above. Likewise, the specific reactivity of starting materials may vary according to and depending upon the particular substituents present or the conditions of manufacture, and such expected variations or differences in the results are contemplated in accordance with the objects and practices of the present invention. It is intended, therefore, that the invention be defined by the scope of the claims which follow and that such claims be interpreted as broadly as is reasonable.

It is further to be understood that all values are approximate, and are provided for description. Patents, patent applications, publications, product descriptions, and protocols are cited throughout this application, the disclosures of which are incorporated herein by reference in their entireties for all purposes.

What is claimed is:

1. A process for preparing a compound of formula (IA):

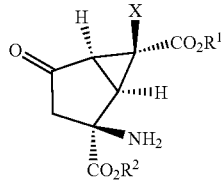

(IA)

wherein $R^1$ and $R^2$ are each selected from the group consisting of
(1) hydrogen,
(2) $C_{1-10}$ alkyl,
(3) $C_{3-8}$ cycloalkyl, and
(4) —$(CH_2)_n$-phenyl
wherein n is 1 or 2, and said alkyl, cycloalkyl and phenyl are unsubstituted or substituted with one or more halogen, hydroxy, $C_{1-6}$ alkyl or $C_{1-6}$ alkoxy;
X is selected from the group consisting of
(1) halogen, and
(2) hydrogen; or
pharmaceutically acceptable salts thereof,
comprising:
(A) oxidizing a compound of formula (II):

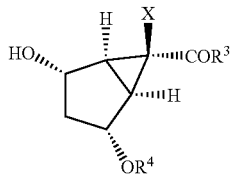

(II)

wherein $R^3$ is selected from the group consisting of
(1) —OH,
(2) —O—$R^a$, and
(3) —$NR^bR^c$,
wherein $R^a$ is selected from the group consisting of
(a) $C_{1-10}$ alkyl, and
(b) $C_{3-8}$ cycloalkyl,
and $R^a$ is unsubstituted or substituted with one or more
(i) $C_{1-10}$ alkoxy,
(ii) hydroxy,
(iii) halogen,
(iv) $SR^d$,
(v) aryl, unsubstituted or substituted with one or more hydroxy, $C_{1-10}$ alkoxy, $C_{1-10}$ alkyl or halogen, and
(vii) $NR^eR^f$;
$R^b$, $R^c$, $R^e$ and $R^f$ are selected from the group consisting of
(a) halogen
(b) $C_{1-10}$ alkyl, and
(c) $C_{3-8}$ cycloalkyl,
and when $R^b$, $R^c$, $R^e$ and $R^f$ are $C_{1-10}$ alkyl or $C_{3-8}$ cycloalkyl, said $C_{1-10}$ alkyl and $C_{3-8}$ cycloalkyl are unsubstituted or substituted with one or more
(i) hydroxy,
(ii) $C_{1-10}$ alkoxy,
(iii) $SR^d$, (iv) aryl, unsubstituted or substituted with one or more hydroxy, $C_{1-10}$ alkoxy, $C_{1-10}$ alkyl or halogen, and
(vi) $NR^gR^h$;
wherein $R^g$ and $R^h$ are hydrogen, $C_{1-10}$ alkyl or $C_{3-8}$ cycloalkyl;
$R^d$ is hydrogen or $C_{1-10}$ alkyl; and
$R^4$ is selected from the group consisting of
(1) hydrogen,
(2) $C_{1-10}$ alkyl,
(3) Si—$(R^9)(R^{10})(R^{11})$,
(4) C(=O)—$R^{12}$, wherein $R^{12}$ is selected from the group consisting of
(a) $C_{1-10}$ alkyl,
(b) $C_{1-10}$ perfluoroalkyl, and
(c) phenyl which is substituted or unsubstituted with one or more substituents selected from the group consisting of nitro, halogen, $C_{1-10}$ alkyl, and $C_{1-10}$ alkoxy,
(5) $CH_2$-phenyl, wherein said phenyl is unsubstituted or substituted with one or more substituents selected from the group consisting of nitro, halogen, $C_{1-10}$ alkyl and $C_{1-10}$ alkoxy,
(6) $(CH_2)_p$—O—$(CH_2)_q$—X'—$R^{14}$,
(7) tetrahyropyranyl,
wherein $R^9$, $R^{10}$ and $R^{11}$ are each $C_{1-10}$ alkyl or phenyl, and $R^{14}$ is selected from the group consisting of
(a) hydrogen,
(b) $C_{1-10}$ alkyl,
p is 1 or 2;
q is an integer selected from 1-10; and
X' is O or a bond;
to form a compound of formula (IV):

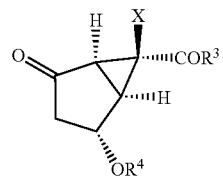

(IV)

(B) deprotecting the compound of formula (IV) to form a compound of formula (V):

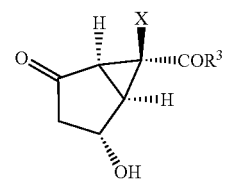

(V)

(C) reacting the compound of formula (V) with a compound of formula (VI):

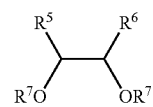

(VI)

wherein R⁵ and R⁶ are each independently selected from the group consisting of
  (1) C$_{1-10}$ alkyl,
  (2) C$_{3-8}$ cycloalkyl, and
  (3) (CH$_2$)$_m$ phenyl,
wherein m is 0, 1 or 2, and
R⁷ is selected from the group consisting of
  (1) hydrogen, and
  (2) Si—(R⁹)(R¹⁰)(R¹¹), wherein R⁹, R¹⁰ and R¹¹ are each C$_{1-10}$ alkyl or phenyl;
to give a compound of formula (VII):

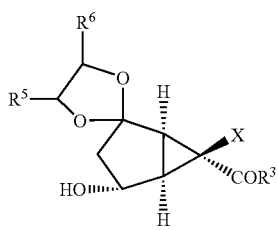
(VII)

(D) oxidizing the compound of formula (VII) to give a compound of formula (VIII):

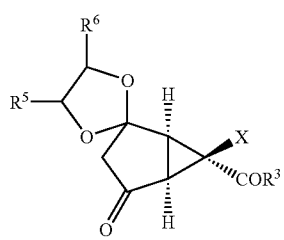
(VIII)

(E) converting the compound of formula (VIII) to a compound of formula (IX):

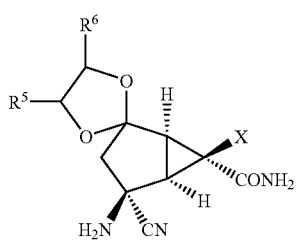
(IX)

and (F) converting the compound of formula (IX) to the compound of formula (IA).

2. The process of claim 1 wherein R⁵ and R⁶ are methyl.
3. The process of claim 1 wherein R⁵ and R⁶ are phenyl.
4. The process of claim 1 wherein R³ is methoxy.
5. The process of claim 1 wherein R¹ and R² are hydrogen.
6. The process of claim 1 wherein R⁷ is trimethylsilyl.
7. The process of claim 1 wherein X is hydrogen.
8. The process of claim 1 wherein X is fluoro.
9. The process of claim 1 wherein R⁴ is tert butyldimethylsilyl.

10. A process for preparing a compound of formula (IA):

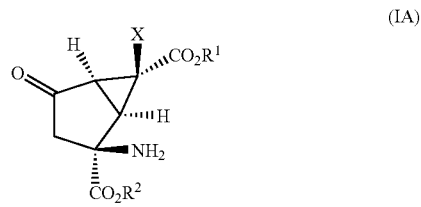
(IA)

wherein R¹ and R² are each selected from the group consisting of
  (1) hydrogen,
  (2) C$_{1-10}$ alkyl,
  (3) C$_{3-8}$ cycloalkyl, and
  (4) —(CH$_2$)$_n$-phenyl
    wherein n is 1 or 2, and said alkyl, cycloalkyl and phenyl are unsubstituted or substituted with one or more halogen, hydroxy, C$_{1-6}$ alkyl or C$_{1-6}$ alkoxy;
X is selected from the group consisting of
  (1) halogen, and
  (2) hydrogen; or
pharmaceutically acceptable salts thereof;
  comprising converting the compound of formula (IX):

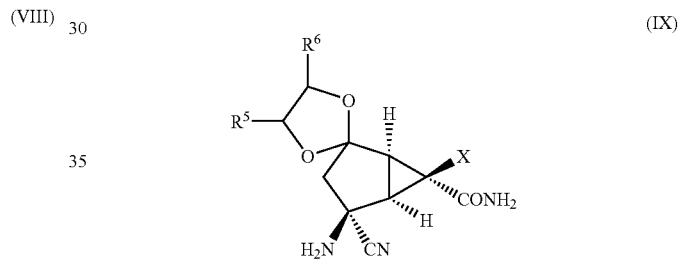
(IX)

wherein R⁵ and R⁶ are each independently selected from the group consisting of
  (1) C$_{1-10}$ alkyl,
  (2) C$_{3-8}$ cycloalkyl, and
  (3) (CH$_2$)$_m$-phenyl,
wherein m is 0, 1 or 2,
to the compound of formula (IA).

11. The process of claim 10 wherein R⁵ and R⁶ are methyl.
12. The process of claim 10 wherein R⁵ and R⁶ are phenyl.
13. The process of claim 10 wherein X is fluoro.
14. The process of claim 10 wherein X is hydrogen.
15. A process for preparing a compound of formula (II):

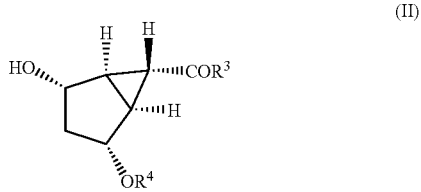
(II)

wherein R³ is selected from the group consisting of
  (1) —OH,
  (2) —O—R$^a$, and (3) —NR$^b$R$^c$,
wherein R$^a$ is selected from the group consisting of
  (a) C$_{1-10}$ alkyl, and
  (b) C$_{3-8}$ cycloalkyl,
and R$^a$ is unsubstituted or substituted with one or more
  (i) C$_{1-10}$ alkoxy,
  (ii) hydroxy,
  (iii) halogen,
  (iv) SR$^d$,
  (v) aryl, unsubstituted or substituted with one or more hydroxy, C$_{1-10}$ alkoxy, C$_{1-10}$ alkyl or halogen,
  (vii) NR$^e$R$^f$;
R$^b$, R$^c$, R$^e$ and R$^f$ are selected from the group consisting of
  (a) hydrogen,
  (b) C$_{1-10}$ alkyl, and
  (c) C$_{3-8}$ cycloalkyl, and when R$^b$, R$^c$, R$^e$ or R$^f$ are C$_{1-10}$ alkyl or C$_{3-8}$ cycloalkyl, said C$_{1-10}$ alkyl and C$_{3-8}$ cycloalkyl are unsubstituted or substituted with one or more
    (i) hydroxy,
    (ii) C$_{1-10}$ alkoxy,
    (iii) SR$^d$,
    (iv) aryl, unsubstituted or substituted with one or more hydroxy, C$_{1-10}$ alkoxy, C$_{1-10}$ alkyl or halogen, and
    (vi) NR$^g$R$^h$;
wherein R$^g$ and R$^h$ are hydrogen, C$_{1-10}$ alkyl or C$_{3-8}$ cycloalkyl;
R$^d$ is hydrogen or C$_{1-10}$ alkyl;
X is selected from the group consisting of
  (1) halogen, and
  (2) hydrogen;
R$^4$ is selected from the group consisting of
  (1) hydrogen,
  (2) C$_{1-10}$ alkyl,
  (3) Si—(R$^9$)(R$^{10}$)(R$^{11}$),
  (4) C(=O)—R$^{12}$, wherein R$^{12}$ is selected from the group consisting of
    (a) C$_{1-10}$ alkyl,
    (b) C$_{1-10}$ perfluoroalkyl, and
    (c) phenyl which is substituted or unsubstituted with one or more substituents selected from the group consisting of nitro, halogen, C$_{1-10}$ alkyl, and C$_{1-10}$ alkoxy,
  (5) CH$_2$-phenyl, wherein said phenyl is unsubstituted or substituted with one or more substituents selected from the group consisting of nitro, halogen, C$_{1-10}$ alkyl and C$_{1-10}$ alkoxy,
  (6) (CH$_2$)$_p$—O—(CH$_2$)$_q$ X'—R$^{14}$
  (7) tetrahyropyranyl,
    wherein R$^9$, R$^{10}$ and R$^{11}$ are each C$_{1-10}$ alkyl or phenyl, and R$^{14}$ is selected from the group consisting of
    (a) hydrogen,
    (b) C$_{1-10}$ alkyl,
  p is 1 or 2;
  q is an integer of from 1-10; and
  X' is O or a bond;

comprising:
(A) converting a compound of formula (X):

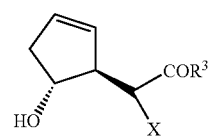

to a compound of formula (XI):

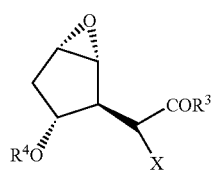

and (B) reacting a compound of formula (XI) with a base in the presence of a Lewis acid to give a compound of formula (II).

16. The process of claim 15 wherein the conversion of a compound of formula (X) to a compound of formula (XI) comprises the step of subjecting a compound of formula (X) to epoxidation in the presence of a peroxide source and a catalytic amount of VO(acac)$_2$.

17. The process of claim 15 wherein the conversion of a compound of formula (X) to a compound of formula (XI) comprises treating the compound of formula (X) with a halogenating agent, followed by treatment with a base.

18. The process of claim 15 wherein X is fluoro.

19. The process of claim 15 wherein X is hydrogen.

20. The process of claim 15, further comprising the step of oxidizing the compound of formula (II) to form a compound of formula (IV)

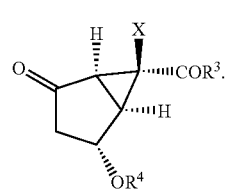

21. The process of claim 20 wherein X is fluoro.
22. The process of claim 20 wherein X is hydrogen.
23. A process for preparing a compound of formula (XII)

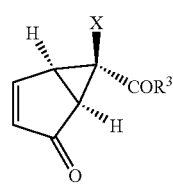

wherein R$^3$ is selected from the group consisting of
  (1) —OH,
  (2) —O—R$^a$, and (3) —NR$^b$R$^c$,
wherein R$^a$ is selected from the group consisting of
  (a) C$_{1-10}$ alkyl, and
  (b) C$_{3-8}$ cycloalkyl,
    and R$^a$ is unsubstituted or substituted with one or more
    (i) C$_{1-10}$ alkoxy,
    (ii) hydroxy,
    (iii) halogen,
    (iv) SR$^d$,
    (v) aryl, unsubstituted or substituted with one or more hydroxy, C$_{1-10}$ alkoxy, C$_{1-10}$ alkyl or halogen,
    (vii) NR$^e$R$^f$;
R$^b$, R$^c$, R$^e$ and R$^f$ are selected from the group consisting of
(a) hydrogen,
(b) C$_{1-10}$ alkyl, and
(c) C$_{3-8}$ cycloalkyl,
  and when R$^b$, R$^c$, R$^e$ and R$^f$ are C$_{1-10}$ alkyl or C$_{3-8}$ cycloalkyl, said C$_{1-10}$ alkyl and C$_{3-8}$ cycloalkyl are unsubstituted or substituted with one or more
  (i) hydroxy,
  (ii) C$_{1-10}$ alkoxy,
  (iii) SR$^d$,
  (iv) aryl, unsubstituted or substituted with one or more hydroxy, C$_{1-10}$ alkoxy, C$_{1-10}$ alkyl or halogen, and
  (vi) NR$^g$R$^h$;
  wherein R$^g$ and R$^h$ are hydrogen, C$_{1-10}$ alkyl or C$_{3-8}$ cycloalkyl;
R$^d$ is hydrogen or C$_{1-10}$ alkyl;
X is selected from the group consisting of
  (1) halogen, and
  (2) hydrogen;
comprising:
(A) converting a compound of formula (II)

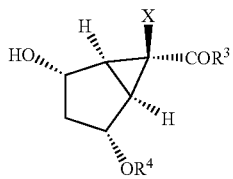

wherein R$^4$ is selected from the group consisting of
  (1) hydrogen,
  (2) C$_{1-10}$ alkyl,
  (3) Si—(R$^9$)(R$^{10}$)(R$^{11}$),
  (4) C(=O)—R$^{12}$, wherein R$^{12}$ is selected from the group consisting of
    (a) C$_{1-10}$ alkyl,
    (b) C$_{1-10}$ perfluoroalkyl, and
    (c) phenyl which is substituted or unsubstituted with one or more substituents selected from the group consisting of nitro, halogen, C$_{1-10}$ alkyl, and C$_{1-10}$ alkoxy,
  (5) CH$_2$-phenyl, wherein said phenyl is unsubstituted or substituted with one or more substituents selected from the group consisting of nitro, halogen, C$_{1-10}$ alkyl and C$_{1-10}$ alkoxy,
  (6) (CH$_2$)$_p$—O—(CH$_2$)$_q$—X'—R$^{14}$,
  (7) tetrahyropyranyl,
    wherein R$^9$, R$^{10}$ and R$^{11}$ are each C$_{1-10}$ alkyl or phenyl, and R$^{14}$ is selected from the group consisting of
    (a) hydrogen,
    (b) C$_{1-10}$ alkyl,
    p is 1 or 2;
    q is an integer of from 1-10; and
    X' is O or a bond;
to a compound of formula (XIII)

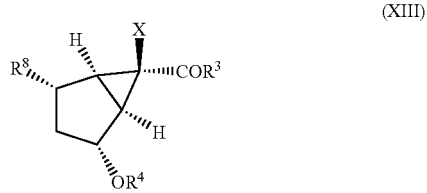

wherein R$^8$ is selected from the group consisting of
  (1) halogen, and
  (2) O—SO$_2$—R$^{12}$, wherein R$^{12}$ is selected from the group consisting of
    (a) C$_{1-10}$ alkyl,
    (b) C$_{1-10}$ perfluoroalkyl, and
    (c) phenyl which is substituted or unsubstituted with one or more substituents selected from the group consisting of nitro, halogen, C$_{1-10}$ alkyl, and C$_{1-10}$ alkoxy,
(B) removing R$^4$ to form a compound of formula (XIV)

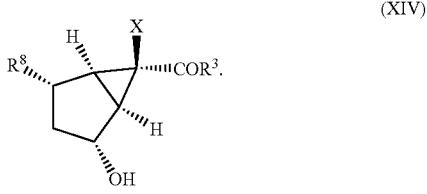

and (C) oxidizing the compound of formula (XIV) to form the compound of formula (XII).

24. The process of claim 23 wherein R$^3$ is methoxy.

25. A process for preparing a compound of formula (XII')

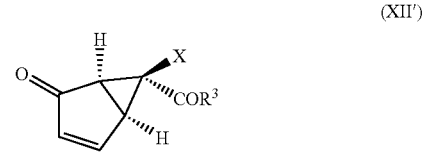

wherein R$^3$ is selected from the group consisting of
  (1) —OH,
  (2) —O—R$^a$, and
  (3) —NR$^b$R$^c$,
    wherein R$^a$ is selected from the group consisting of
    (a) C$_{1-10}$ alkyl, and
    (b) C$_{3-8}$ cycloalkyl,
      and R$^a$ is unsubstituted or substituted with one or more
      (i) C$_{1-10}$ alkoxy,
      (ii) hydroxy,
      (iii) halogen,
      (iv) SR$^d$, (v) aryl, unsubstituted or substituted with one or more hydroxy, $C_{1-10}$ alkoxy, $C_{1-10}$ alkyl or halogen,
(vii) $NR^eR^f$;
$R^b$, and $R^c$, $R^e$ and $R^f$ are selected from the group consisting of
(a) hydrogen,
(b) $C_{1-10}$ alkyl, and
(c) $C_{3-8}$ cycloalkyl,
and when $R^b$, $R^c$, $R^e$ and $R^f$ are $C_{1-10}$ alkyl or $C_{3-8}$ cycloalkyl, said $C_{1-10}$ alkyl and $C_{3-8}$ cycloalkyl are unsubstituted or substituted with one or more
(i) hydroxy,
(ii) $C_{1-10}$ alkoxy,
(iii) $SR^d$,
(iv) aryl, unsubstituted or substituted with one or more hydroxy, $C_{1-10}$ alkoxy, $C_{1-10}$ alkyl or halogen,
(vi) $NR^gR^h$;
wherein $R^g$ and $R^h$ are selected from the group consisting of hydrogen, $C_{1-10}$ alkyl or $C_{3-8}$ cycloalkyl;
$R^d$ is hydrogen or $C_{1-10}$ alkyl;
X is selected from the group consisting of
(1) halogen, and
(2) hydrogen; and
$R^4$ is selected from the group consisting of
(1) hydrogen,
(2) $C_{1-10}$ alkyl,
(3) Si—$(R^9)(R^{10})(R^{11})$,
(4) C(=O)—$R^{12}$, wherein $R^{12}$ is selected from the group consisting of
(a) $C_{1-10}$ alkyl,
(b) $C_{1-10}$ perfluoroalkyl, and
(c) phenyl which is substituted or unsubstituted with one or more substituents selected from the group consisting of nitro, halogen, $C_{1-10}$ alkyl, and $C_{1-10}$ to alkoxy,
(5) $CH_2$-phenyl, wherein said phenyl is unsubstituted or substituted with one or more substituents selected from the group consisting of nitro, halogen, $C_{1-10}$ and $C_{1-10}$ alkoxy,
(6) $(CH_2)_p$—O—$(CH_2)_q$—X'—$R^{14}$,
(7) tetrahyropyranyl,
wherein $R^9$, $R^{10}$ and $R^{11}$ are each $C_{1-10}$ alkyl or phenyl, and $R^{14}$ is selected from the group consisting of
(a) hydrogen,
(b) $C_{1-10}$ alkyl;
p is 1 or 2;
q is an integer of from 1-10; and
X' is O or a bond;
comprising converting a compound of formula (IV)

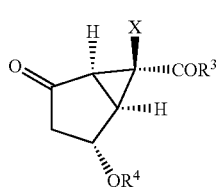

(IV)

to a compound of formula (XII').

26. A compound of formula (VII):

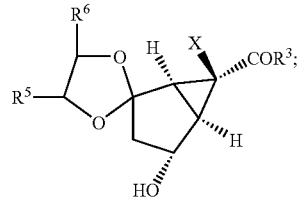

(VII)

wherein $R^3$ is selected from the group consisting of
(1) —OH,
(2) —O—$R^a$, and
(3) —$NR^bR^c$,
wherein $R^a$ is selected from the group consisting of
(a) $C_{1-10}$ alkyl, and
(b) $C_{3-8}$ cycloalkyl,
and $R^a$ is unsubstituted or substituted with one or more
(i) $C_{1-10}$ alkoxy,
(ii) hydroxy,
(iii) halogen,
(iv) $SR^d$,
(v) aryl, unsubstituted or substituted with one or more hydroxy, $C_{1-10}$ alkoxy, $C_{1-10}$ alkyl or halogen,
(vii) $NR^eR^f$;
$R^b$, $R^c$, $R^e$ and $R^f$ are selected from the group consisting of
(a) hydrogen,
(b) $C_{1-10}$ alkyl, and
(c) $C_{3-8}$ cycloalkyl,
and when $R^b$, $R^c$, $R^e$ and $R^f$ are $C_{1-10}$ alkyl or $C_{3-8}$ cycloalkyl, said $C_{1-10}$ alkyl and $C_{3-8}$ cycloalkyl are unsubstituted or substituted with one or more
(i) hydroxy,
(ii) $C_{1-10}$ alkoxy,
(iii) $SR^d$,
(iv) aryl, unsubstituted or substituted with one or more hydroxy, $C_{1-10}$ alkoxy, $C_{1-10}$ alkyl or halogen,
(vii) $NR^gR^h$;
wherein $R^g$ and $R^h$ are selected from the group consisting of hydrogen, $C_{1-10}$ alkyl or $C_{3-8}$ cycloalkyl
$R^d$ is hydrogen or $C_{1-10}$ alkyl;
$R^5$ and $R^6$ are independently selected from the group consisting of
(1) $C_{1-10}$ alkyl,
(2) $C_{3-8}$ cycloalkyl, and
(3) $(CH_2)_m$-phenyl,
wherein m is 0, 1 or 2; and
X is selected from the group consisting of
(1) halogen, and
(2) hydrogen;
or salts thereof.

27. A compound of formula (VIII):

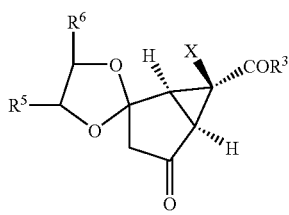

wherein R³ is selected from the group consisting of
(1) —OH,
(2) —O—Rᵃ, and
(3) —NRᵇRᶜ,
wherein Rᵃ is selected from the group consisting of
(a) $C_{1-10}$ alkyl, and
(b) $C_{3-8}$ cycloalkyl,
and Rᵃ is unsubstituted or substituted with one or more
(i) $C_{1-10}$ alkoxy,
(ii) hydroxy,
(iii) halogen,
(iv) SRᵈ,
(v) aryl, unsubstituted or substituted with one or more hydroxy, $C_{1-10}$ alkoxy, $C_{1-10}$ alkyl or halogen,
(vii) NRᵉRᶠ;
Rᵇ, Rᶜ, Rᵉ and Rᶠ are selected from the group consisting of
(a) hydrogen,
(b) $C_{1-10}$ alkyl, and
(c) $C_{3-8}$ cycloalkyl,
and when Rᵇ, Rᶜ, Rᵉ and Rᶠ are $C_{1-10}$ alkyl or $C_{3-8}$ cycloalkyl, said $C_{1-10}$ alkyl and $C_{3-8}$ cycloalkyl are unsubstituted or substituted with one or more
(i) hydroxy,
(ii) $C_{1-10}$ alkoxy,
(iii) SRᵈ,
(iv) aryl, unsubstituted or substituted with one or more hydroxy, $C_{1-10}$ alkoxy, $C_{1-10}$ alkyl or halogen, and
(vi) NRᵍRʰ;
wherein Rᵍ and Rʰ are hydrogen, $C_{1-10}$ alkyl or $C_{3-8}$ cycloalkyl;
Rᵈ is hydrogen or $C_{1-10}$ alkyl;
R⁵ and R⁶ are independently selected from the group consisting of
(1) $C_{1-10}$ alkyl,
(2) $C_{3-8}$ cycloalkyl, and
(3) $(CH_2)_m$ phenyl,
wherein m is 0, 1 or 2; and
X is selected from the group consisting of
(1) halogen, and
(2) hydrogen;
or salts thereof.

28. A compound of formula (IX):

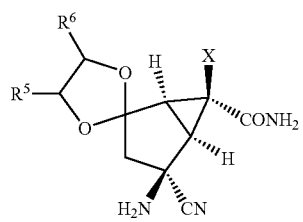

wherein R⁵ and R⁶ are independently selected from the group consisting of
(1) $C_{1-10}$ alkyl,
(2) $C_{3-8}$ cycloalkyl, and
(3) $(CH_2)_m$-phenyl,
wherein m is 0, 1 or 2; and
X is selected from the group consisting of
(1) halogen, and
(2) hydrogen;
or salts thereof.

29. A compound of formula (XA):

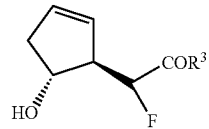

wherein R³ is selected from the group consisting of
(1) —OH,
(2) —O—Rᵃ, and
(3) —NRᵇRᶜ,
wherein Rᵃ is selected from the group consisting of
(a) $C_{1-10}$ alkyl, and
(b) $C_{3-8}$ cycloalkyl,
and Rᵃ is unsubstituted or substituted with one or more
(i) $C_{1-10}$ alkoxy,
(ii) hydroxy,
(iii) halogen,
(iv) SRᵈ,
(v) aryl, unsubstituted or substituted with one or more hydroxy, $C_{1-10}$ alkoxy, $C_{1-10}$ alkyl or halogen,
(vii) NRᵉRᶠ;
Rᵇ, Rᶜ, Rᵉ and Rᶠ are selected from the group consisting of
(a) hydrogen,
(b) $C_{1-10}$ alkyl, and
(c) $C_{3-8}$ cycloalkyl,
and when Rᵇ, Rᶜ, Rᵉ and Rᶠ are $C_{1-10}$ alkyl or $C_{3-8}$ cycloalkyl, said $C_{1-10}$ alkyl and $C_{3-8}$ cycloalkyl are unsubstituted or substituted with one or more
(i) hydroxy,
(ii) $C_{1-10}$ alkoxy,
(iii) SRᵈ,
(iv) aryl, unsubstituted or substituted with one or more hydroxy, $C_{1-10}$ alkoxy, $C_{1-10}$ alkyl or halogen, and
(vi) NRᵍRʰ;

wherein $R^g$ and $R^h$ are hydrogen, $C_{1-10}$ alkyl or $C_{3-8}$ cycloalkyl;
$R^d$ is hydrogen or $C_{1-10}$ alkyl;
or salts thereof.

30. A compound of formula (XI):

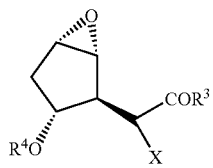

(XI)

wherein $R^3$ is selected from the group consisting of
(1) —OH,
(2) —O—$R^a$, and
(3) —$NR^bR^c$,
  wherein $R^a$ is selected from the group consisting of
    (a) $C_{1-10}$ alkyl, and
    (b) $C_{3-8}$ cycloalkyl,
      and $R^a$ is unsubstituted or substituted with one or more
        (i) $C_{1-10}$ alkoxy,
        (ii) hydroxy,
        (iii) halogen,
        (iv) $SR^d$,
        (v) aryl, unsubstituted or substituted with one or more hydroxy, $C_{1-10}$ alkoxy, $C_{1-10}$ alkyl or halogen,
        (vii) $NR^eR^f$;
$R^b$, $R^c$, $R^e$ and $R^f$ are selected from the group consisting of
  (a) hydrogen,
  (b) $C_{1-10}$ alkyl, and
  (c) $C_{3-8}$ cycloalkyl,
    and when $R^b$, $R^c$, $R^e$ and $R^f$ are $C_{1-10}$ alkyl or $C_{3-8}$ cycloalkyl, said $C_{1-10}$ alkyl and $C_{3-8}$ cycloalkyl are unsubstituted or substituted with one or more
      (i) hydroxy,
      (ii) $C_{1-10}$ alkoxy,
      (iii) $SR^d$,
      (iv) aryl, unsubstituted or substituted with one or more hydroxy, $C_{1-10}$ alkoxy, $C_{1-10}$ alkyl or halogen, and
      (vi) $NR^gR^h$;
    wherein $R^g$ and $R^h$ are hydrogen, $C_{1-10}$ alkyl or $C_{3-8}$ cycloalkyl;
$R^d$ is hydrogen or $C_{1-10}$ alkyl;
$R^4$ is selected from the group consisting of
  (1) hydrogen,
  (2) $C_{1-10}$ alkyl,
  (3) Si—$(R^9)(R^{10})(R^{11})$,
  (4) C(=O)—$R^{12}$, wherein $R^{12}$ is selected from the group consisting of
    (a) $C_{1-10}$ alkyl,
    (b) $C_{1-10}$ perfluoroalkyl, and
    (c) phenyl which is substituted or unsubstituted with one or more substituents selected from the group consisting of nitro, halogen, $C_{1-10}$ alkyl, and $C_{1-10}$ alkoxy,
  (5) $CH_2$-phenyl, wherein said phenyl is unsubstituted or substituted with one or more substituents selected from the group consisting of nitro, halogen, $C_{1-10}$ alkyl and $C_{1-10}$ alkoxy,
  (6) $(CH_2)_p$—O—$(CH_2)_q$—X'—$R^{14}$,
  (7) tetrahyropyranyl,
    wherein $R^9$, $R^{10}$ and $R^{11}$ are each $C_{1-10}$ alkyl or phenyl, and $R^{14}$ is selected from the group consisting of
      (a) hydrogen,
      (b) $C_{1-10}$ alkyl,
    p is 1 or 2;
    q is an integer of from 1-10; and
    X' is O or a bond;
X is selected from the group consisting of
  (1) halogen, and
  (2) hydrogen;
or salts thereof.

31. A compound of formula (IVA):

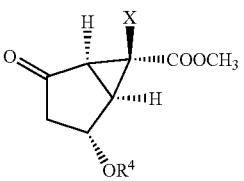

(IVA)

wherein X is selected from the group consisting of
  (1) halogen, and
  (2) hydrogen; and
$R^4$ is selected from the group consisting of
  (1) hydrogen,
  (2) $C_{1-10}$ alkyl,
  (3) Si—$(R^9)(R^{10})(R^{11})$,
  (4) C(=O)—$R^{12}$, wherein $R^{12}$ is selected from the group consisting of
    (a) $C_{1-10}$ alkyl,
    (b) $C_{1-10}$ perfluoroalkyl, and
    (c) phenyl which is substituted or unsubstituted with one or more substituents selected from the group consisting of nitro, halogen, $C_{1-10}$ alkyl, and $C_{1-10}$ alkoxy,
  (5) $CH_2$-phenyl, wherein said phenyl is unsubstituted or substituted with one or more substituents selected from the group consisting of nitro, halogen, $C_{1-10}$ alkyl and $C_{1-10}$ alkoxy,
  (6) $(CH_2)_p$—O—$(CH_2)_q$—X'—$R^{14}$, and
  (7) tetrahyropyranyl,
    wherein $R^9$, $R^{10}$ and $R^{11}$ are each $C_{1-10}$ alkyl or phenyl, and $R^{14}$ is selected from the group consisting of
      (a) hydrogen,
      (b) $C_{1-10}$ alkyl,
    p is 1 or 2;
    q is an integer of from 1-10; and
    X' is O or a bond;
or salts thereof.

32. A compound of formula (II):

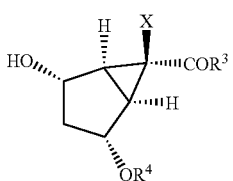

(II)

wherein $R^3$ is selected from the group consisting of
  (1) —OH,
  (2) —O—$R^a$, and (3) —NR$^b$R$^c$,
  wherein R$^a$ is selected from the group consisting of
  (a) C$_{1-10}$ alkyl, and
  (b) C$_{3-8}$ cycloalkyl,
    and R$^a$ is unsubstituted or substituted with one or more
    (i) C$_{1-10}$ alkoxy,
    (ii) hydroxy,
    (iii) halogen,
    (iv) SR$^d$,
    (v) aryl, unsubstituted or substituted with one or more hydroxy, C$_{1-10}$ alkoxy, C$_{1-10}$ alkyl or halogen,
    (vii) NR$^e$R$^f$;
R$^b$, R$^c$, R$^e$ and R$^f$ are selected from the group consisting of
  (a) hydrogen,
  (b) C$_{1-10}$ alkyl, and
  (c) C$_{3-8}$ cycloalkyl,
    and when R$^b$, R$^c$, R$^e$ and R$^f$ are C$_{1-10}$ alkyl or C$_{3-8}$ cycloalkyl, said C$_{1-10}$ alkyl and C$_{3-8}$ cycloalkyl are unsubstituted or substituted with one or more
    (i) hydroxy,
    (ii) C$_{1-10}$ alkoxy,
    (iii) SR$^d$,
    (iv) aryl, unsubstituted or substituted with one or more hydroxy, C$_{1-10}$ alkoxy, C$_{1-10}$ alkyl or halogen, and
    (vi) NR$^g$R$^h$;
  wherein R$^g$ and R$^h$ are hydrogen, C$_{1-10}$ alkyl or C$_{3-8}$ cycloalkyl;
R$^d$ is hydrogen or C$_{1-10}$ alkyl;
R$^4$ is selected from the group consisting of
  (1) hydrogen,
  (2) C$_{1-10}$ alkyl,
  (3) Si—(R$^9$)(R$^{10}$)(R$^{11}$),
  (4) C(=O)—R$^{12}$, wherein R$^{12}$ is selected from the group consisting of
    (a) C$_{1-10}$ alkyl,
    (b) C$_{1-10}$ perfluoroalkyl, and
    (c) phenyl which is substituted or unsubstituted with one or more substituents selected from the group consisting of nitro, halogen, C$_{1-10}$ alkyl, and C$_{1-10}$ alkoxy,
  (5) CH$_2$-phenyl, wherein said phenyl is unsubstituted or substituted with one or more substituents selected from the group consisting of nitro, halogen, C$_{1-10}$ alkyl and C$_{1-10}$ alkoxy,
  (6) (CH$_2$)$_p$—O—(CH$_2$)$_q$—X'—R$^{14}$, and
  (7) tetrahydropyranyl,
wherein R$^9$, R$^{10}$ and R$^{11}$ are each C$_{1-10}$ alkyl or phenyl, and
R$^{14}$ is selected from the group consisting of
  (a) hydrogen,
  (b) C$_{1-10}$ alkyl,
p is 1 or 2;
q is an integer of from 1-10; and
X' is O or a bond;
X is selected from the group consisting of
  (1) halogen, and
  (2) hydrogen;
or salts thereof.

* * * * *